(12) United States Patent
Mynott et al.

(10) Patent No.: US 7,833,963 B2
(45) Date of Patent: Nov. 16, 2010

(54) COMPONENT OF BROMELAIN

(75) Inventors: Tracey L. Mynott, Richmond (GB); Christian Engwerda, Richmond (GB); Keith Peek, Ewloe (GB)

(73) Assignee: Sarantis Pty Ltd, Stones Corner, Queensland (AU)

( * ) Notice: Subject to any disclaimer, the term of this patent is extended or adjusted under 35 U.S.C. 154(b) by 636 days.

(21) Appl. No.: 10/452,210

(22) Filed: Jun. 3, 2003

(65) Prior Publication Data

US 2004/0057948 A1 Mar. 25, 2004

Related U.S. Application Data

(60) Continuation of application No. 09/750,210, filed on Dec. 29, 2000, now abandoned, which is a division of application No. 09/382,688, filed on Aug. 25, 1999, now abandoned, which is a continuation of application No. 09/380,095, filed as application No. PCT/GB98/00590 on Feb. 25, 1998, now abandoned.

(30) Foreign Application Priority Data

| Feb. 25, 1997 | (GB) | ................... 9703827.7 |
| Feb. 25, 1997 | (GB) | ................... 9703850.9 |
| Feb. 28, 1997 | (GB) | ................... 9704252.7 |
| Mar. 25, 1997 | (GB) | ................... 9706119.6 |

(51) Int. Cl.
*A61K 38/00* (2006.01)
*C07K 14/00* (2006.01)
*C07K 1/00* (2006.01)

(52) U.S. Cl. ....................... 514/2; 530/350; 530/412

(58) Field of Classification Search ................ None
See application file for complete search history.

(56) References Cited

U.S. PATENT DOCUMENTS

| 4,485,095 | A |   | 11/1984 | Fujisaki et al. |
| 5,106,621 | A | * | 4/1992 | Rowan et al. ............ 424/94.65 |
| 5,223,406 | A |   | 6/1993 | Ransberger et al. |
| 5,260,074 | A |   | 11/1993 | Sipos |
| 5,324,514 | A |   | 6/1994 | Sipos |
| 5,356,625 | A |   | 10/1994 | Ying |
| 5,387,517 | A |   | 2/1995 | Cini |
| 5,460,812 | A |   | 10/1995 | Sipos |
| 5,484,609 | A |   | 1/1996 | Ko |
| 5,578,304 | A |   | 11/1996 | Sipos |
| 5,578,310 | A | * | 11/1996 | M'Timkulu et al. ......... 424/401 |
| 5,597,564 | A |   | 1/1997 | Ying |
| 5,824,305 | A |   | 10/1998 | Mynott |
| 5,928,640 | A |   | 7/1999 | Mynott |
| 6,335,427 | B1 |  | 1/2002 | Mynott et al. |
| 2002/0188107 | A1 | | 12/2002 | Mynott et al. |

FOREIGN PATENT DOCUMENTS

| DE | 4302060 A1 | 7/1994 |
| EP | 0313346 A2 | 4/1989 |
| EP | 0576938 A1 | 1/1994 |
| JP | 59-225122 A | 12/1984 |
| JP | 02-16977 A | 1/1990 |
| JP | 2001-513635 A | 9/2001 |
| JP | 2001-513636 A | 9/2001 |
| WO | WO 85/03438 A1 | 8/1985 |
| WO | WO 88/01506 A1 | 3/1988 |
| WO | WO 93/01800 A1 | 2/1993 |
| WO | WO 94/00147 A1 | 1/1994 |
| WO | WO 95/00169 A1 | 1/1995 |
| WO | WO 96/00082 * | 1/1996 |
| WO | WO 97/24138 A2 | 1/1997 |
| WO | WO 98/38291 A1 | 9/1998 |
| WO | WO 98/38319 A1 | 9/1998 |
| WO | WO 98/38320 A1 | 9/1998 |
| WO | WO 99/00141 A1 | 1/1999 |
| WO | WO 00/14253 A1 | 3/2000 |

OTHER PUBLICATIONS

Taussig and Batkin, J. Ethnopharmacol., 1988, vol. 22(2), pp. 191-203.*
Maurer, 2001, Cell. Mol. Life Sci., vol. 58, pp. 1234-1245.*
Napper et al., Biochem. J., 1994, vol. 301, pp. 727-735.*
Bocchino et al., Int. J. Tuberc Lung Dis., 2005, 9(4):375-383. (abstract).*
Roberts et al., oncogene, 2007, 26(22):3291-3310.*
Yao et al., Acta Biochim. Biophys. Sin. (shanghai), 2006, 38(4):249-253 (Abstract).*
Hodge et al., Eur. J. Cancer, 2005, 41(16):2502-2512.*
Purcell et al., Shock, 2006, 25(2):135-40 (Abstract).*

(Continued)

*Primary Examiner*—Elizabeth C. Kemmerer
*Assistant Examiner*—Xiaozhen Xie
(74) *Attorney, Agent, or Firm*—Leydig, Voit & Mayer, Ltd.

(57) ABSTRACT

The invention relates to a component of bromelain which is largely responsible for the ability of bromelain to interrupt the MAP kinase cascade. The component contains ananain and comosain and is useful in the treatment or prevention of diseases and conditions mediated by T cell activation or by activation of the MAP kinase pathway.

2 Claims, 15 Drawing Sheets

OTHER PUBLICATIONS

Hayrinen-Immonen, Scand. J. Dent. Res., 1992, 100(4):222-227 (Abstract).*
Barshes et al., Front. Biosci. 2004, 9:411-20.*
Lee et al., J. Leukoc. Biol., vol. 59(2):152-157.*
Harrach et al., J. Prot. Chem., 1995, vol. 14(1):41-52.*
Belham et al., Biochem. J., 320: 939-946 (1996).
Bliska et al., Cell, 73: 903-920 (1993).
Cantrell, Annu. Rev. Immunol., 14: 259-274 (1996).
Filippova et al., Anal. Biochem, 143: 293-297 (1984).
Galan et al., Nature, 357: 588-589 (1992).
Harrach et al., J. Protein Chemistry, 14(1): 41-52 (1995).
Maurer et al., Planta Medica, 377-381 (1988).
Munzig et al., FEBS Letters, 351: 215-218 (1994).
Perandones et al., J. Immunol, 151 (7): 3521-3529 (1993).
Rowan et al., Archives of Biochem. and BioPhys., 267(1): 262-270 (1988).
Rowan et al., Methods in Enzymology, 244: 555-568 (1994).
Taussig et al., Planta Medica, 538-539 (1985).
Vouret-Craviari et al., Biochem. J., 289: 209-214 (1993).
Avruch et al., Trends Biochem Sci., 19: 279-283 (1994).
Fang, ASM News, 63: 668-673 (1997).
Fox, Intl. Immunol., 5: 343-330 (1993).
Garbin et al., Intl. J. Oncol., 5: 197-203 (1994).
Gillis et al., J. Immunol., 120: 2027-2032 (1978).
Hibbs, Res. Immunol., 142: 565-569 (1991).
Izquierdo et al., Mol. Cell. Biol., 12: 3305-3312 (1992).
Izquierdo et al., J. Exp. Med., 178: 1199-1208 (1993).
June et al., J. Immunol., 144: 1591-1599 (1990).
June et al., PNAS, 87: 7722-7726 (1990).
Kaye et al., Infection and Immunity, 60: 4335-4342 (1992).
Kelland et al., Cancer Res., 53: 2581-2586 (1993).
Lotz-Winter, Planta Medica, 56(3): 249-253 (1990).
Lowry et al., J. Biol. Chem., 193: 265-275 (1951).
Muta et al., EMBL/GenBank/DDBJ Databases, Accession No. O23791, submitted Jan. 1993, updated Jan. 1, 1998, created Jan. 24, 2006.
Muta et al., EMBL/GenBank/DDBJ Databases, Accession No. O23801, submitted Oct. 1994, updated Jan. 1, 1998, created Jan. 1, 1998.
Ota et al., J. Biochem., 98: 219-228 (1985).
Rayter et al., EMBO J., 11: 4549-4556 (1992).
Roach et al., Infection and Immunity, 59: 3935-3944 (1991).
Sagar et al., Cancer Treatment Rev., 21: 159-181 (1995).
Seifert et al., Acta Pharm. Technol., 34: 55-62 (1988).
Truneh et al., Nature, 31(3): 318-320 (1985).
Mynott et al., Gastroenterology, 113: 175-184 (1997).
Barlow, Burns, 20(6): 487-90 (1994).
Church et al., Clin. Microbiol. Rev., 19(2): 403-34 (Apr. 2006).

* cited by examiner

A.

B.

A.

B

COMPONENT OF BROMELAIN

CROSS REFERENCE TO RELATED APPLICATIONS

The present application is a continuation of U.S. application Ser. No. 09/750,210, filed Dec. 29, 2000 (now abandoned), which was published Aug. 1, 2002 as U.S. Application Publication No. US-2002-0102253-A1, which is a divisional of U.S. application Ser. No. 09/382,688, filed Aug. 25, 1999 (now abandoned), which is a continuation of U.S. application Ser. No. 09/380,095, filed Aug. 25, 1999 (now abandoned), which is the U.S. national phase application of International Application No. PCT/GB98/00590, filed Feb. 25, 1998, which was published under PCT Article 21(2) in English as WIPO Publication No. WO 98/38291 on Sep. 3, 1998; which Applications claim priority under 35 U.S.C. §119 to the following United Kingdom Patent Application Nos. GB 9703850.9, filed Feb. 25, 1997, GB 9703827.7, filed Feb. 25, 1997, GB 9704252.7, filed Feb. 28, 1997, and GB 9706119.6, filed Mar. 25, 1997.

The present invention relates to a component of bromelain. In particular, the invention relates to the use of this bromelain component in medicine, particularly as an anticancer agent and an immunosuppressive agent.

Stem bromelain (bromelain) is the collective name for the proteolytic enzymes found in the tissues of the plant Bromeliaceae. It is a mixture of various moieties derived from the stem of the pineapple plant (*Ananas comosus*). Bromelain is known to contain at least five proteolytic enzymes but also non-proteolytic enzymes, including an acid phosphatase and a peroxidase; it may also contain amylase and cellulase activity. In addition, various other components are present.

Bromelain has previously been used in the treatment of a variety of conditions including inflammation and, in particular, it has been used in the treatment of diarrhoea. The use of bromelain in the treatment of infectious diarrhoea is described in WO-A-9301800, where it is suggested that bromelain works by destroying intestinal receptors for pathogens by proteolysis, and in WO-A-8801506, which teaches that bromelain detaches pathogens from intestinal receptors.

Taussig et al, *Planta Medica,* 1985, 538-539 and Maurer et al, *Planta Medica,* 1988, 377-381 both suggest that bromelain may be of use in inhibiting tumour growth. U.S. Pat. No. 5,223,406, DE-A-4302060 and JP-A-59225122 also teach the use of bromelain in the treatment of cancer. U.S. Pat. No. 5,223,406 teaches that bromelain is capable of inducing tumour necrosis factor (TNF) while DE-A4302060 teaches that bromelain can prevent metastasis by the structural modification of the tumour surface protein CD44.

In WO-A-9400147, various experiments were described which demonstrate that proteolytic enzymes and, in particular, bromelain, are capable of inhibiting secretion. The application also discloses that bromelain can reduce toxin binding activity and can inhibit the secretory effect of toxins such as heat labile toxin (LT) and cholera toxin (CT) and also toxins such as heat stable toxin (ST). This is in spite of the fact that ST has a very different mode of action from LT and CT. These observations were explained by the fact that one component of the bromelain mixture, stem bromelain protease, appears to be capable of modulating cyclic nucleotide pathways and this is discussed further in WO-A-9500169. In addition, bromelain has also been demonstrated to inhibit secretion caused by the calcium dependent pathway.

The present inventors have studied the varied biological effects of bromelain and, in particular, its effects in a well documented model of intracellular signal transduction, namely T cell receptor (TCR)/CD3 signalling and IL-2 production. Significant progress over recent years has led to the understanding of biochemical events which occur following TCR engagement (reviewed Cantrell, *Annu. Rev. Immunol.* 14, 259-274, (1996)), therefore TCR signalling provides an excellent model for elucidation of the effects of biologically active compounds. Effective T cell activation requires two signals. The first signal is generated by the TCR/CD3 complex after engagement with antigen peptide presented by the major histocompatibility complex (MHC) expressed on antigen presenting cells (APC) (Cantrell, 1996). The second, costimulatory signal is generated by ligation of CD28 receptors on T cells with the B7 family of ligands on APC. A key element in the signalling pathway involved in transducing receptor-initiated signals to the nucleus is the family of mitogen-activated protein kinases (MAPk). The best studied of these kinases are the extracellular signal-regulated protein kinases (ERK)-1 and ERK-2 (also referred to as $p44^{MAPk}$ and $p42^{MAPk}$, respectively). ERK's are serine/threonine kinases that are activated when phosphorylated on tyrosine and threonine residues. In vitro, this activation is reversed if either residue is dephosphorylated. A relatively newly discovered member of the MAPk family are c-Jun $NH_2$-terminal kinases (JNKs) which exist as 46 kDa and 55 kDa forms that also require phosphorylation for activation. ERK activation is dependent on $p56^{Lck}$ and coupling of the TCR/CD3 complex to $p21^{Ras}$, with subsequent activation of the Raf-1/MEK1/ERK kinase cascade. JNK activation also requires p21%, as well as signals generated by the CD28 costimulatory receptor which activate GTP (guanosine triphosphate)-binding proteins (such as Rac1 or Cdc42) that induce the PAK/MEKK/SEK/JNK kinase cascade. Activated ERK phosphorylates Elk-1, which in turn, mediates induction of c-fos activity following phosphorylation of c-jun by JNK. Activated c-fos and c-jun combine to form the AP-1 protein required for IL-2 synthesis. The above events are summarised in FIG. 1. All the above-mentioned signalling events require tyrosine phosphorylation, as inhibitors of protein tyrosine kinases (PTKs) inhibit many events associated with TCR stimulation, including T cell activation and IL-2 production.

In WO-A-9600082, we showed that bromelain could inhibit tyrosine phosphorylation and activation of ERK-2 in T cells stimulated via the TCR, or with combined phorbol ester plus calcium ionophore. We have now found that, in association with decreased ERK activity, bromelain decreased IL-2, IL-4 and IFN-γ mRNA accumulation in T cells stimulated with phorbol ester and ionophore, but did not affect cytokine mRNA accumulation in cells stimulated via the TCR. This data suggests the existence of a TCR-activated, ERK-independent pathway involved in cytokine production in T cells.

From the prior art, it is clear that bromelain is a mixture which has a variety of different physiological effects. Not all of the components of the bromelain mixture have been characterised and so, except for stem bromelain protease, whose activity we have described, it is not clear which of the components is responsible for which of the various different effects of bromelain. This is, of course, a major disadvantage if the bromelain mixture is to be administered as a pharmaceutical because while one component of bromelain might give the desired effect, there may well be unwanted side effects arising from the action of some other component of the bromelain mixture.

It would therefore be beneficial if individual components of bromelain giving rise to particular medicinal activities could be isolated and administered separately so as to lessen the possibility of side effects. We have now identified an active fraction of crude bromelain which is responsible for its ability to inhibit ERK activation, and therefore block the MAP kinase pathway. Although not a single protein, this fraction consists of only a few components and so the possibility of side effects when it is administered to patients is greatly reduced compared with crude bromelain.

The fraction of the invention, which the inventors have designated CCS, may be isolated from the bromelain mixture by conventional methods, for example by chromatography. High performance liquid chromatograpy (HPLC) is suitable for the purpose and particularly good separation of bromelain proteins may be achieved by fast protein liquid chromatography (FPLC™) using a column packing material such as S-sepharose. As will be described in more detail in the examples, in chromatography on S-sepharose using a linear gradient of 0 to 0.8M sodium chloride in acetate buffer over 300 ml, the protein of the present invention was the last double peak off the column.

In a first aspect of the present invention, there is provided a component of bromelain which contains proteins having molecular weights of about 15.07 kDa, 25.85 kDa and 27.45 kDa as determined by SDS-PAGE, has isoelectric points of 10.4 and 10.45 and is obtainable by the following method:
i. dissolving bromelain in acetate buffer at pH 5.0;
ii. separating the components of the bromelain by fast flow high performance liquid chromatography on S-sepharose eluting with a linear gradient of 0 to 0.8 M sodium chloride in acetate buffer over 300 ml;
iii. collecting the fraction corresponding to the final double peak off the column; and
iv. isolating the protein from the fraction collected in (iii).

This fraction, termed CCS, has been found to have a number of potentially useful activities. Firstly, we have found that it blocks ERK-2 phosphorylation, and therefore the MAP kinase cascade. In addition, it blocked IL-2 production and CD4$^+$ T cell proliferation. However, CCS did not affect splenocyte proliferation, which suggests that it has a selective mode of action. CCS also differentially blocked growth of human tumour cell lines including ovarian, lung, colon, melanoma and breast tumours. The differential activity of CCS against the different cell lines further suggests that CCS has a selective mode of action and that it may also act as an anti-cancer agent. The inhibitory effect of CCS on ERK-2 is dependent on its proteolytic activity, since E-64, a selective cysteine protease inhibitor, could abrogate the effect of CCS.

Although in WO-A-9724138, we stated that proteases in general are capable of decreasing MAP kinase activation, we have now found that this is not the case as trypsin does not abrogate T cell signalling and, indeed, in other studies, has been shown to increase MAPk activation (Belham et al, 1996, Biochem. J., 320, 939-946). Thrombin, a protease involved in the blood coagulation cascade, has also been shown to increase MAP kinase activation (Vouret-Craviari et al, 1993, Biochem. J., 289, 209-214). The inventors have now also shown that other proteases contained within the crude bromelain mixture do not block the activation of the MAP kinase pathway.

It is possible that the effects of CCS on the MAP kinase pathway in T cells are mediated by specific proteolytic effects at the cell surface. It is known that bromelain cleaves the CD45 RA isoform and selectively removes other surface molecules from human PBMCs. Bromelain also partially removes CD4 from T cell surfaces. Since CD45 and CD4 play an obligate stimulatory role in TCR-mediated T cell activation, CCS may interfere with TCR signalling by affecting these molecules. Although the importance of CD45 and CD4 is well recognised for TCR-initiated signal transduction, it is possible to bypass their requirements for T cell activation by the use of phorbol ester and calcium ionophore. Use of combined phorbol esters and ionophore restores normal function to T cells which have been made refractory to TCR stimulation by the use of tyrosine kinase inhibitors or which are CD45 or p56$^{Lck}$ deficient.

However, in the present study, the inventors have shown that normal function is not restored to T cells pre-treated with CCS when they are treated with PMA plus ionophore. The inhibitory effect of CCS on ERK-2 is thus not thought to be mediated via effects on CD45 or CD4 on T cells. CCS possibly affects an as yet unidentified surface molecule, which, in turn, affects the MAP kinase pathway. The inhibitory effect of CCS on cytokine production is thus not thought to be mediated via its effects on CD45 or CD4 on T cells. The inhibitory effect of CCS on T cell signal transduction was not because of toxicity of the compound, since CCS did not affect splenocyte or GA15 cell viability. The viability of the cells was not significantly affected by culture in the presence of CCS for periods of time greater than 48 hours.

Since we have shown that fraction CCS from crude bromelain blocks activation of the MAP kinase pathway and blocks T cell activation, CCS may be of use in the treatment of T cell-mediated diseases.

In addition to its importance for IL-2 production and T cell activation, the MAP kinase pathway is also important for the production of growth factors such as epidermal growth factor (EGF), platelet derived growth factor (PGDF) and insulin-like growth factor (IGF). CCS will therefore block the production of these, and other, growth factors and the production of other cytokines such as IL4, IFN-γ, GM-GSF and many more.

Also, as briefly mentioned above, CCS is likely to be of use in the treatment of cancer.

Thus, CCS may be of use in a method for the treatment or prevention of diseases or conditions mediated by:
i. activation of T cells;
ii. activation of the MAP kinase pathway; or
iii. the production of growth factors or cytokines;
or in the treatment or prevention of cancer.

In a second aspect of the invention, therefore, there is provided a component of bromelain which contains proteins having molecular weights of about 15.07 kDa, 25.85 kDa and 27.45 kDa as determined by SDS-PAGE, has isoelectric points of 10.4 and 10.45 and is obtainable by the following method:
i. dissolving bromelain in acetate buffer at pH 5.0;
ii. separating the components of the bromelain by fast flow high performance liquid chromatography on S-sepharose eluting with a linear gradient of 0 to 0.8 M sodium chloride in acetate buffer over 300 ml;
iii. collecting the fraction corresponding to the final double peak off the column; and
iv. isolating the protein from the fraction collected in (iii)

for use in medicine, particularly in the treatment or prevention of diseases and conditions mediated by:
i. activation of T cells;
ii. activation of the MAP kinase pathway; or
iii. the production of growth factors or cytokines;
or in the treatment or prevention of cancer.

On further analysis of the CCS fraction of bromelain, the present inventors have found that it comprises more than one component. Sequencing of the proteins in the fraction showed that it consists of the cysteine proteases ananain and comosain together with various other components.

Thus, it appears that both ananain and comosain or a mixture of the two may be responsible for the activity of the CCS fraction of bromelain.

In a further aspect of the invention, therefore, there is provided the use of ananain, comosain, a mixture of ananain and comosain or the CCS fraction of bromelain in the preparation of an agent for treatment or prevention of diseases or conditions mediated by:
i. activation of T cells;
ii. activation of the MAP kinase pathway; or
iii. the production of growth factors or cytokines;
or in the treatment or prevention of cancer.

In our earlier application WO-A-9600082 we discussed the inhibition of the MAP kinase cascade by crude bromelain. However, at that time, we were not able to determine which component of the crude bromelain mixture was responsible for this activity although we speculated that it might be stem bromelain protease. We have now discovered that in addition to blocking cyclic nucleotide pathways, stem bromelain protease does have some activity against the MAP kinase pathway. However, it is far less effective in blocking the MAP kinase cascade than the CCS fraction of bromelain of the present invention. Indeed, we have now found that the CCS fraction of bromelain is in the region of ten orders of magnitude more active than stem bromelain protease in blocking MAP kinase activation.

The activation of the MAP kinase pathway in T cells to produce IL-2 and drive T cell clonal expansion is an essential component of the immune response. The absence of this process can have fatal consequences, as can be observed in people with AIDS or genetic mutations which result in T cell defects. However, the activation of T cells can also lead to detrimental consequences. For example, if autoreactive T cells are activated, autoimmune diseases can result. CCS is therefore likely to be of use in the treatment of autoimmune diseases such as rheumatoid arthritis, type-1 diabetes mellitus, multiple sclerosis, Crohn's disease and lupus.

Also, the activation of T cells specific for engrafted tissue can lead to graft or transplant rejection and so CCS may also be of use in preventing this.

The activation of allergen-specific T cells can cause allergic reactions. Inflammatory cytokines and other cellular products, such as histamine, are released from cells following exposure to allergens. The release of histamine and inflammatory cytokines involves the MAP kinase pathway and so blocking of the MAP kinase pathway with CCS is likely to be an effective treatment for allergies.

In addition, CCS is likely to be of use in the prevention of toxic shock and other diseases mediated by over production of bacterial endotoxins. Toxic shock is mediated by the production of lipopolysaccharides (LPS) from gram-negative bacteria. LPS triggers the production of TNF-α and interleukin-1 via activation of the MAP kinase pathway in macrophages. The secretion of these cytokines elicits a cascade of cytokine production from other cells of the immune system (including T cells), which leads to leucocytosis, shock, intravascular coagulation and death.

A further use for CCS is in the prevention of programmed cell death (apoptosis). This is a special event whereby cells are stimulated to destroy their own DNA and die. It is an essential event in most immune responses (to prevent the accumulation of too many cells), but can also have immunosuppressive consequences in some instances, such as in HIV infection and ageing so that too many cells die and there are insufficient left to combat infection (Perandones et al, 1993, *J. Immunol.*, 151, 3521-3529). Because the initiation of apoptosis is dependent on specific cell signalling events, including activation of the MAP kinase pathway, CCS is likely to be effective in blocking apoptosis.

The continual activation of T cells during chronic disease can also lead to pathological consequences, as can be found in certain chronic parasitic infections, such as chronic granulatomas diseases such as tuberculoid leprosy, schistosomiasis and visceral leishmaniasis. Furthermore, the invasion of parasites and pathogens, and their subsequent survival in cells, is dependent on these organisms utilising host cell signalling pathways (Bliska et al, 1993, *Cell*, 73, 903-920). For example, *Salmonella* has been demonstrated to phosphorylate MAP kinase, which allows for the bacteria to become endocytosed by macrophages (Galan et al, 1992, *Nature*, 357, 588-589). The bacteria then proliferate and destroy the cell. Because CCS has been shown to modify host signalling pathways, and, in particular, to inhibit MAP kinase, another of its potential applications could be to inhibit invasion by parasites and pathogens and their survival in cells.

CCS may also be of use for the treatment of cancer and, indeed, we have shown that CCS can block human tumour growth in vitro. The anti-tumour mechanism of action of CCS remains to be determined but seems likely to be a result of the blocking of activation of the ERK-2 pathway.

As mentioned earlier, MAP kinase activation is dependent on $p21^{Ras}$ and Raf-1, which are important oncogenes. $p21^{Ras}$ and Raf-1 proteins help to relay signals from growth factor receptors on the surface of cells to MAP kinases to stimulate cell proliferation or differentiation. Oncogenic (or mutant) $p21^{Ras}$ or Raf-1 genes produce defective proteins that have acquired independence from externally supplied growth factors and, at the same time, may no longer respond to external growth-inhibitory signals. Mutant $p21^{Ras}$ or Raf-1 proteins are thus persistently hyperactive and their unbridled catalytic activity has a detrimental effect on the control of cell growth. Oncogenic $p21^{Ras}$ or Raf-1 genes therefore promote cancer and tumour formation by disrupting the normal controls on cell proliferation and differentiation. Approximately 30% of human cancers have mutations in a $p21^{Ras}$ gene.

Given that signals transmitted by $p21^{Ras}$ and Raf-1 can be blocked via MAP kinase, CCS would be expected to block cancer and tumour growth. The protein fraction of the present invention would therefore be useful for treating many different types of cancer including solid cancers such as ovarian, colon, breast or lung cancer and melanoma as well as non-solid tumours and leukaemia.

The bromelain fraction of the invention will usually be formulated before administration to patients and so, in a further aspect of the invention there is provided a pharmaceutical or veterinary composition comprising the CCS fraction of bromelain together with a pharmaceutically or veterinarily acceptable excipient.

The CCS fraction may be administered by a variety of routes including enteral, for example oral, nasal, buccal, topical or anal administration or parenteral administration, for example by the intravenous, subcutaneous, intramuscular or intraperitoneal routes.

In many cases, the oral route may be preferred as this is often the route which patients find most acceptable. The oral route may be particularly useful if many doses of the protein are required.

When oral administration is chosen, it may be desirable to formulate the CCS fraction in an enteric-coated preparation in order to assist its survival through the stomach. Alternatively, another orally administrable dosage form may be used, for example a syrup, elixir or a hard or soft gelatin capsule, either of which may be enteric coated.

However, under certain circumstances, it may more convenient to use a parenteral route. For parenteral administration, the protein may be formulated in distilled water or another pharmaceutically acceptable solvent or suspending agent.

A suitable dose of the CCS fraction to be administered to a patient may be determined by the clinician. However, as a guide, a suitable dose may be from about 0.5 to 20 mg per kg of body weight. It is expected that in most cases, the dose will be from about 1 to 15 mg per kg of body weight and preferably from 1 to 10 mg per kg of body weight. For a man having a weight of about 70 kg, a typical dose would therefore be from about 70 to 700 mg.

The invention will now be further described with reference to the following examples and to the drawings in which.

Figure 4:
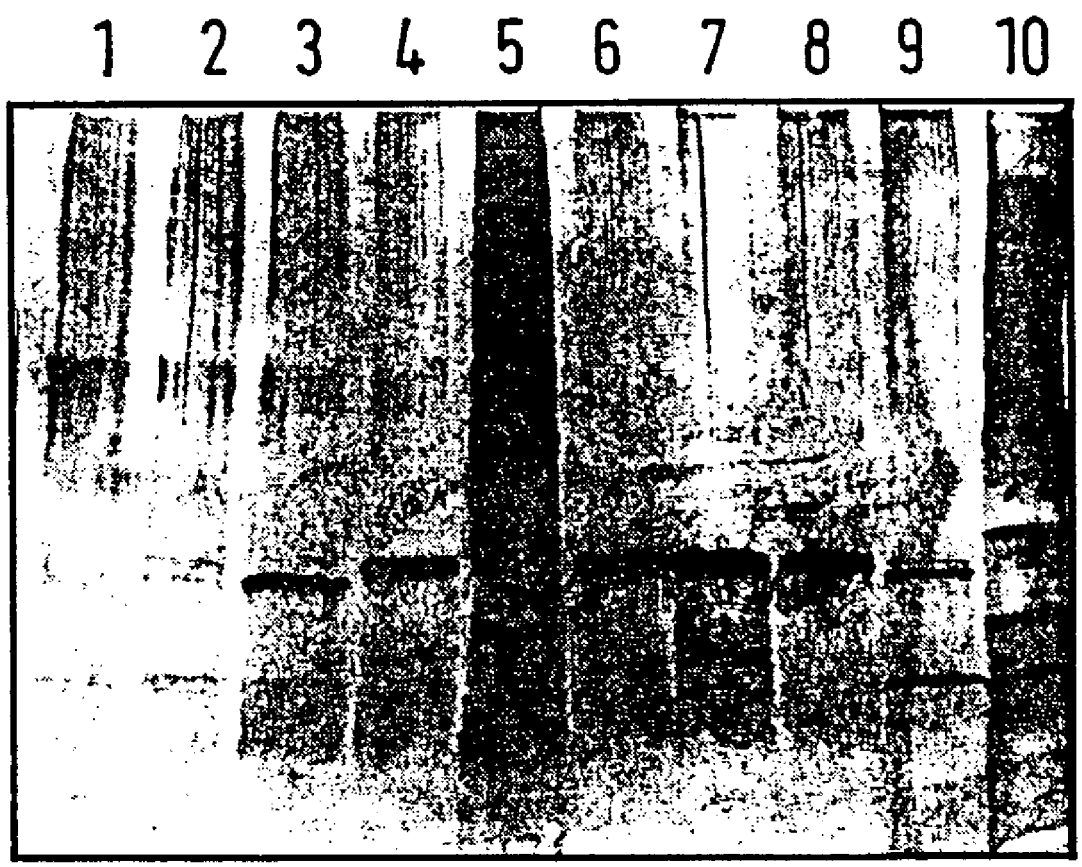

FIG. 4 is an SDS-PAGE of SP Sepharose high performance chromatography pooled fractions run on 4-20% T gradient gels with lanes 1 to 4 and 6 to 9 containing proteins CCT, CCV, CCX and CCZ and CCY, CCW, CCU and CCS respectively and lanes 5 and 10 containing molecular weight markers.

Figure 5:
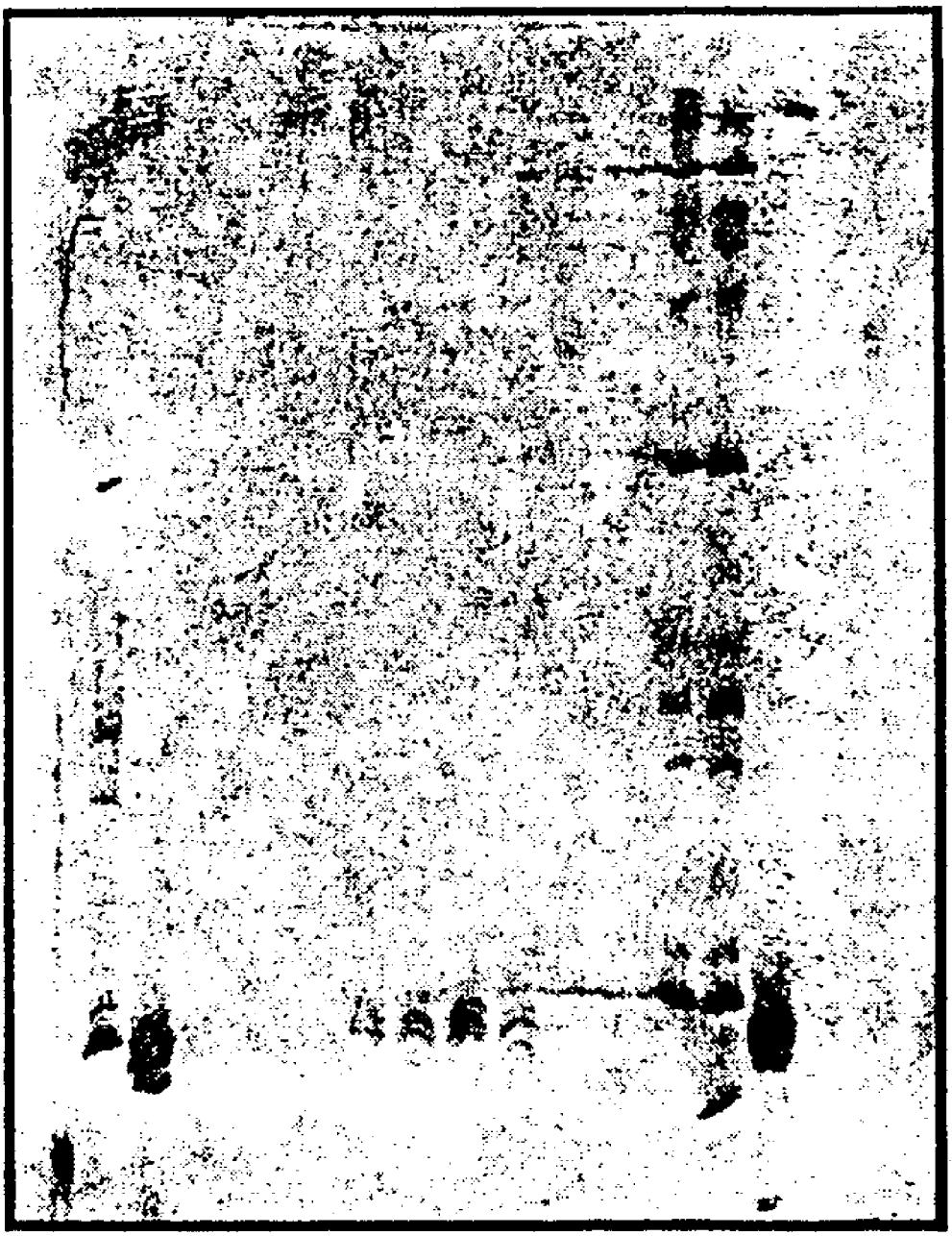

FIG. 5 shows isoelectric focussing of pooled fractions run on pH 3-11 gradient gels with Lanes 1, 11 and 12 showing high IEF markers, Lanes 2 and 13 showing crude bromelain and Lanes 3 to 10 showing proteins CCT, CCV, CCX, CCZ, CCY, CCW, CCU and CCS respectively.

Figure 6:
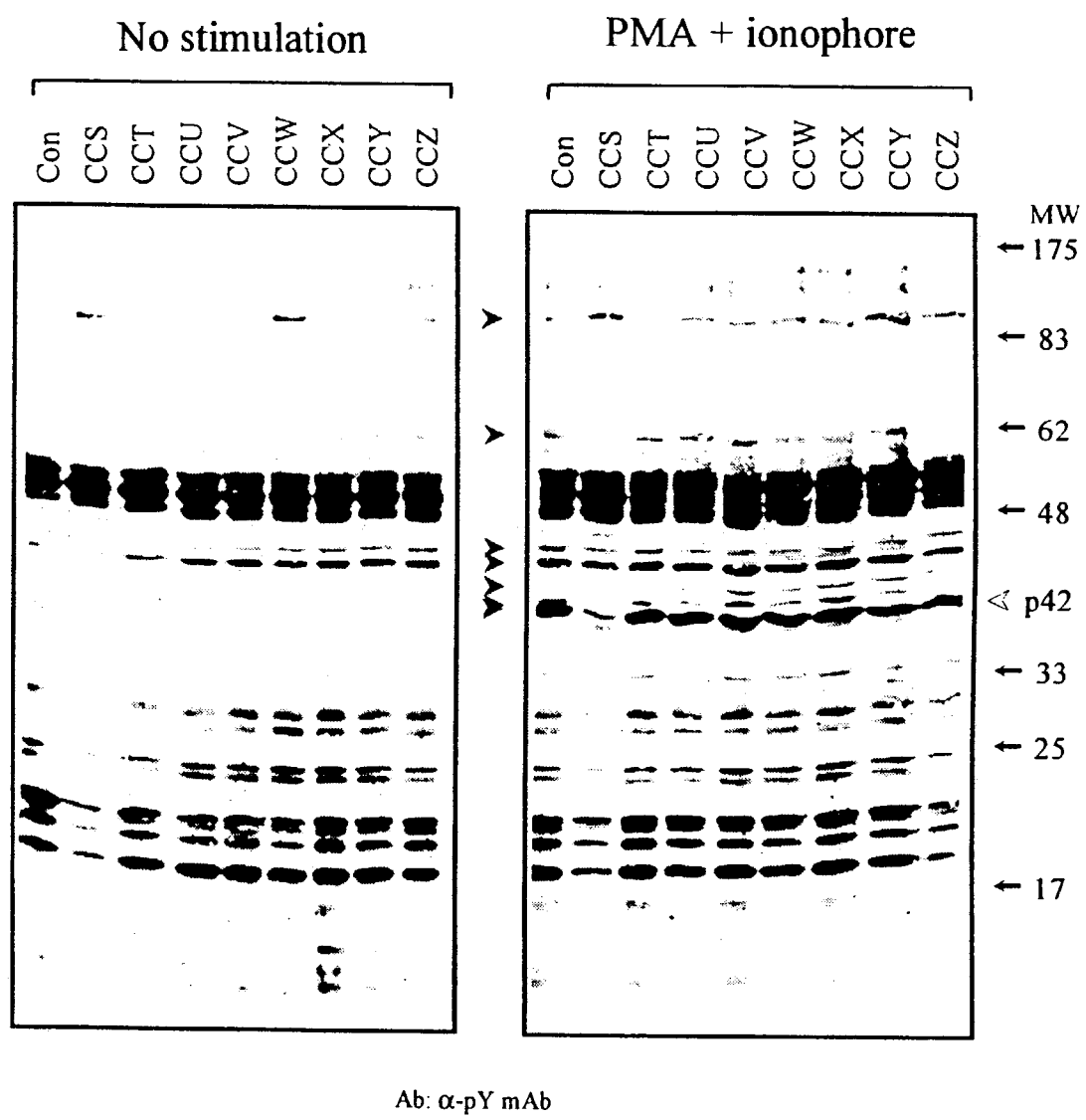

FIG. 6 is a Western blot using anti-phosphotyrosine mAb which demonstrates that CCS reduces tyrosine phosphorylation of p42 kDa (ERK-2) protein. Th0 cells were treated with bromelain fractions (50 μg/ml) for 30 min, washed and then stimulated with combined PMA (20 ng/ml) and ionophore (1 μM) for 5 min. Unstimulated cells served as controls. Cells were then lysed and postnuclear supernatants were subjected to SDS-PAGE and Western blotting. In this figure, closed symbols indicate proteins phosphorylated by combined PMA plus ionophore. Open symbols indicate ERK-2 protein reduced by CCS treatment.

Figure 7:
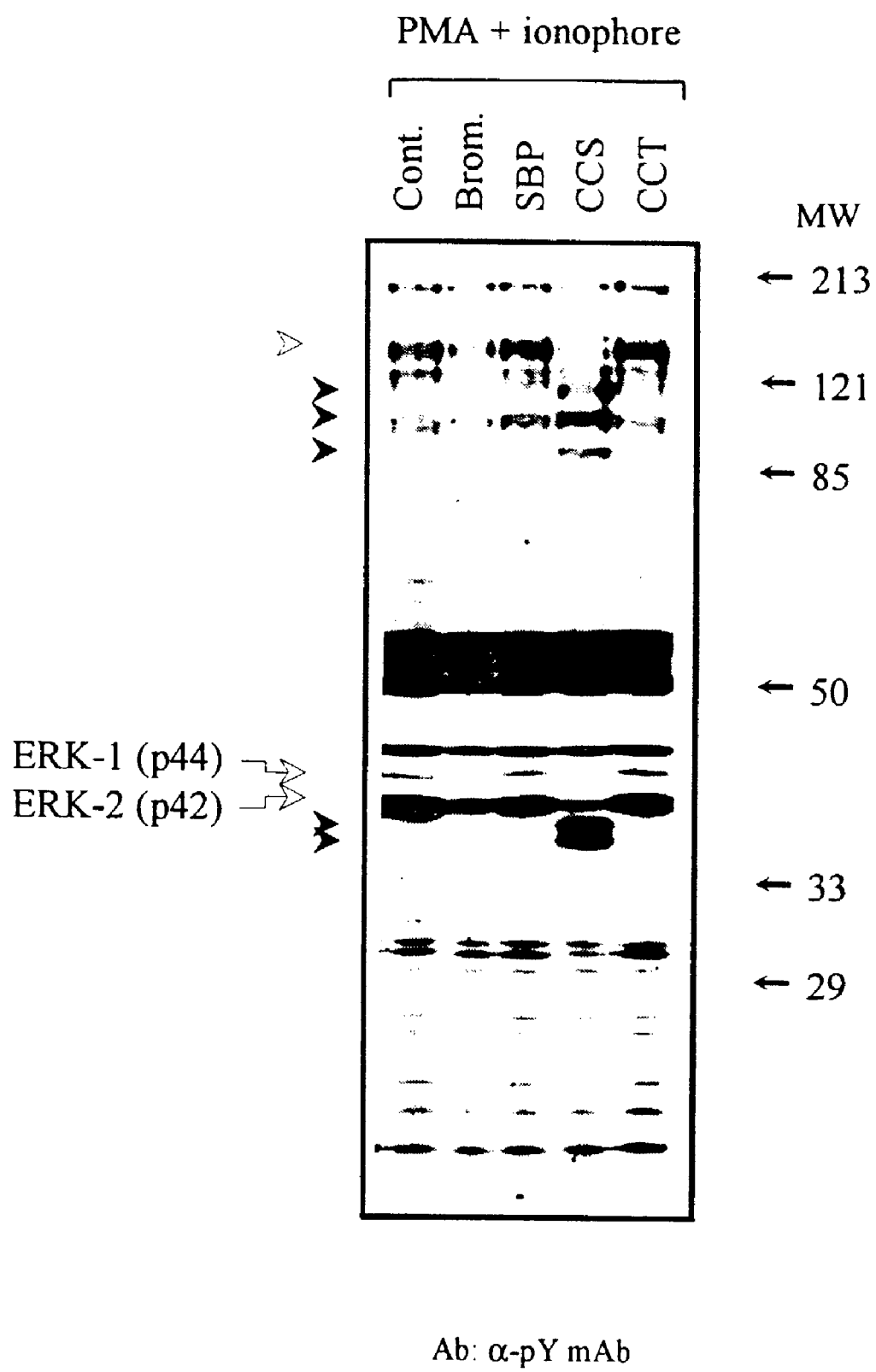

FIG. 7 is a Western blot using anti-phosphotyrosine mab which demonstrates that CCS increases tyrosine phosphorylation of protein substrates. Th0 cells were treated with CCS, crude bromelain (Brom), stem bromelain protease (SBP) or CCT fraction (50 μg/ml) for 30 min, washed and then stimulated with combined PMA (20 ng/ml) and ionophore (1 μM) for 5 min. Unstimulated cells served as controls (Cont). Cells were then lysed and postnuclear supernatants were subjected to SDS-PAGE and Western blotting. In this figure, closed symbols indicate proteins phosphorylated by CCS but not by other treatments. Open symbols indicate phosphoproteins protein reduced by CCS and crude bromelain treatment.

Figure 8:
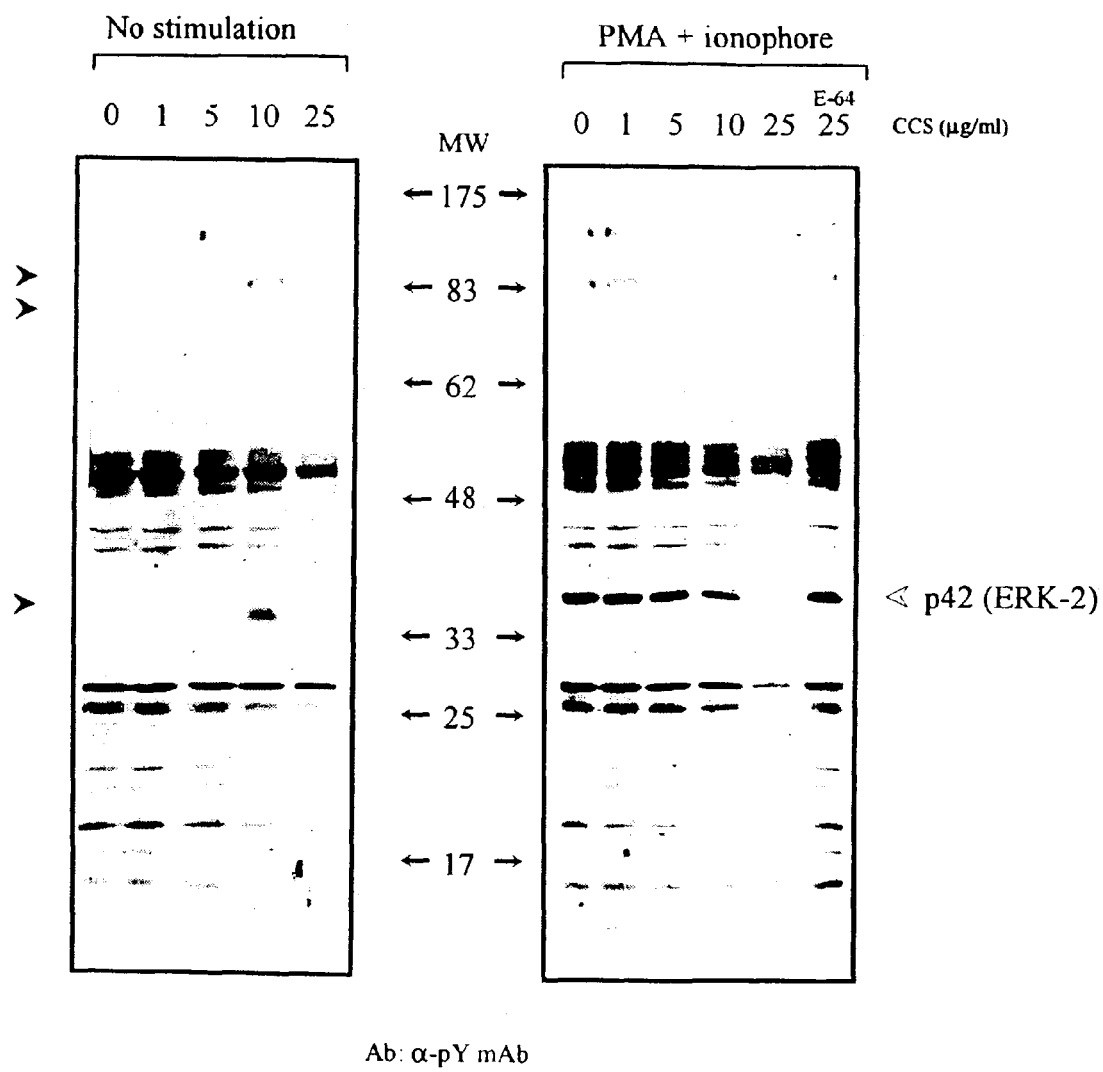

FIG. 8 is a Western blot using anti-phosphotyrosine mAb which shows that the inhibitory effect of CCS on ERK-2 is dependent on its proteolytic activity and occurs in a dose-dependent manner. Th0 cells were treated with CCS (0 to 25 μg/ml) or CCS incubated with the selected protease inhibitor, E-64, for 30 min. Cells were then washed and then stimulated with combined PMA (20 ng/ml) and ionophore (1 μM) for 5 min. Cells were then lysed and postnuclear supernatants were subjected to SDS-PAGE and Western blotting. In this figure, closed symbols indicate proteins phosphorylated by CCS. Open symbols indicate ERK-2 phosphoprotein inhibited by active CCS but not by inactivated CCS.

Figure 9:
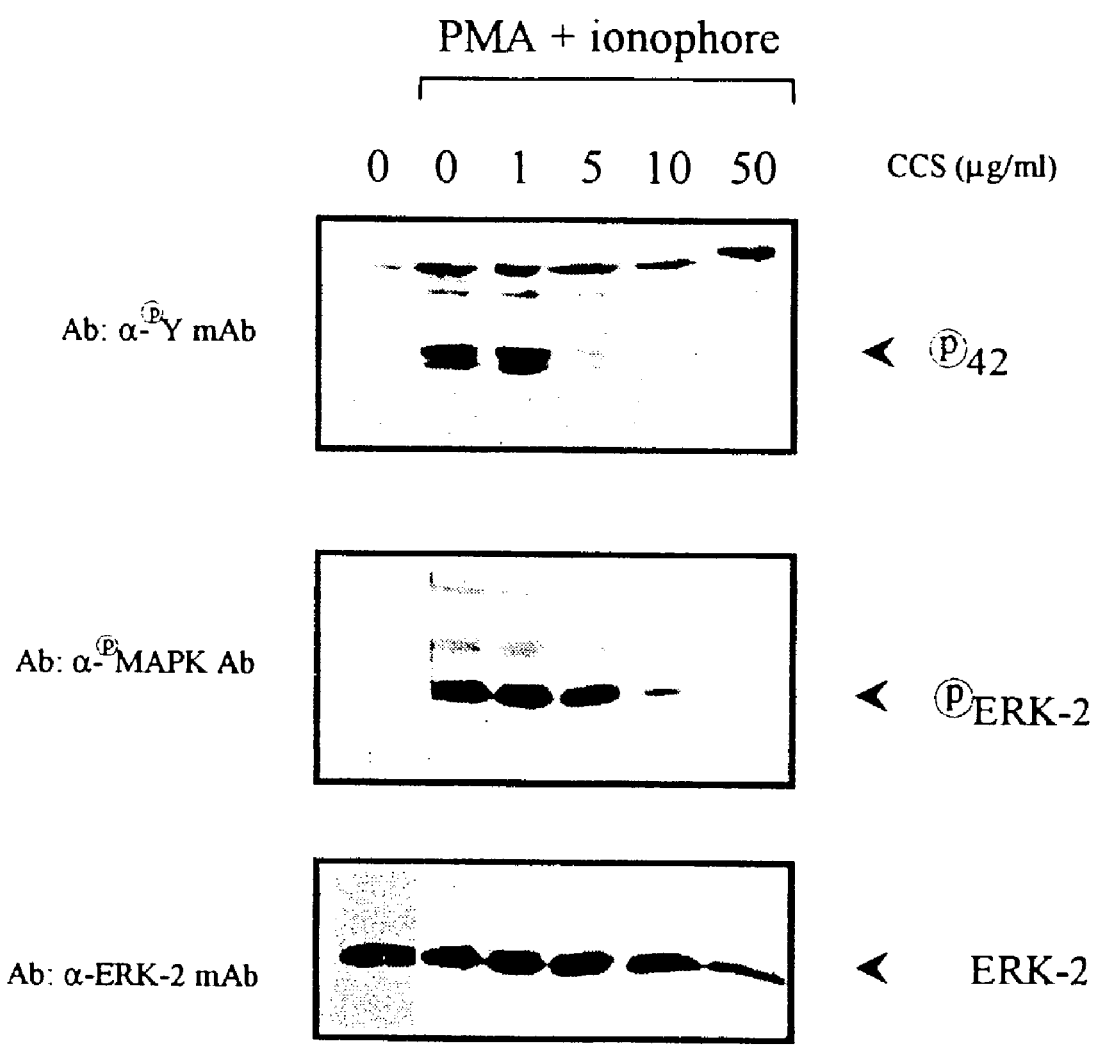
Figure 10:
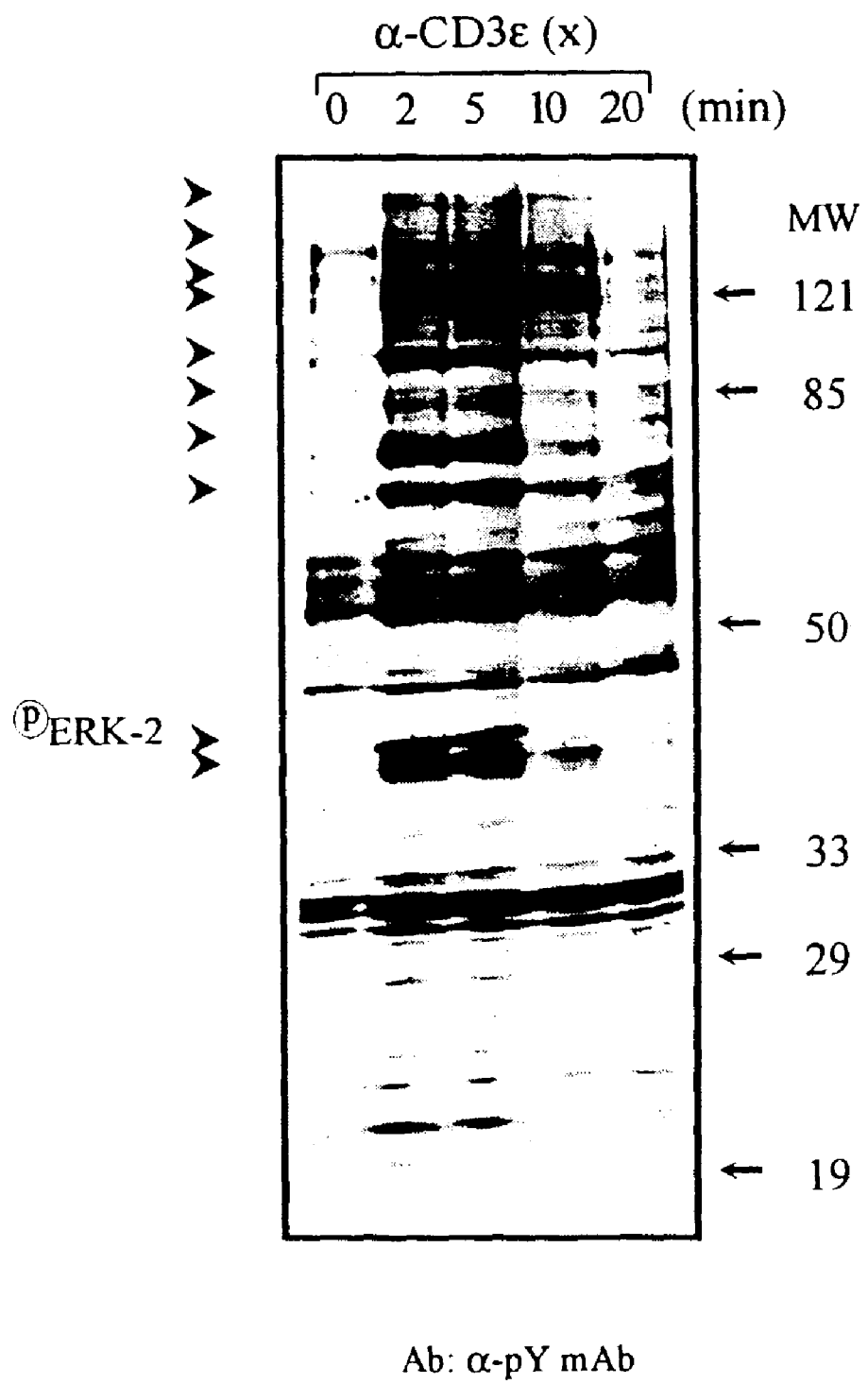

FIG. 9 is an immunoblot which confirms that the 42 kDa phosphoprotein inhibited by CCS is ERK-2. Th0 cells were treated with CCS (50 μg/ml) for 30 min, or untreated, washed and then stimulated with combined PMA (20 ng/ml) and ionophore (1 μM) for 5 min. Cell lysates were immunoblotted with anti-ERK-2 mAB FIG. 10 is a Western blot using anti-phosphotyrosine mAb which shows that crosslinked anti-CD3ε mAb induces tyrosine phosphorylation of multiple proteins. Th0 cells were stimulated with crosslinked anti-CD3ε for 0 to 20 min. Cells were then lysed and postnuclear supernatants were subjected to SDS-PAGE and Western blotting. Closed symbols denote anti-CD3εmAb-induced tyrosine phosphorylated proteins.

Figure 11:
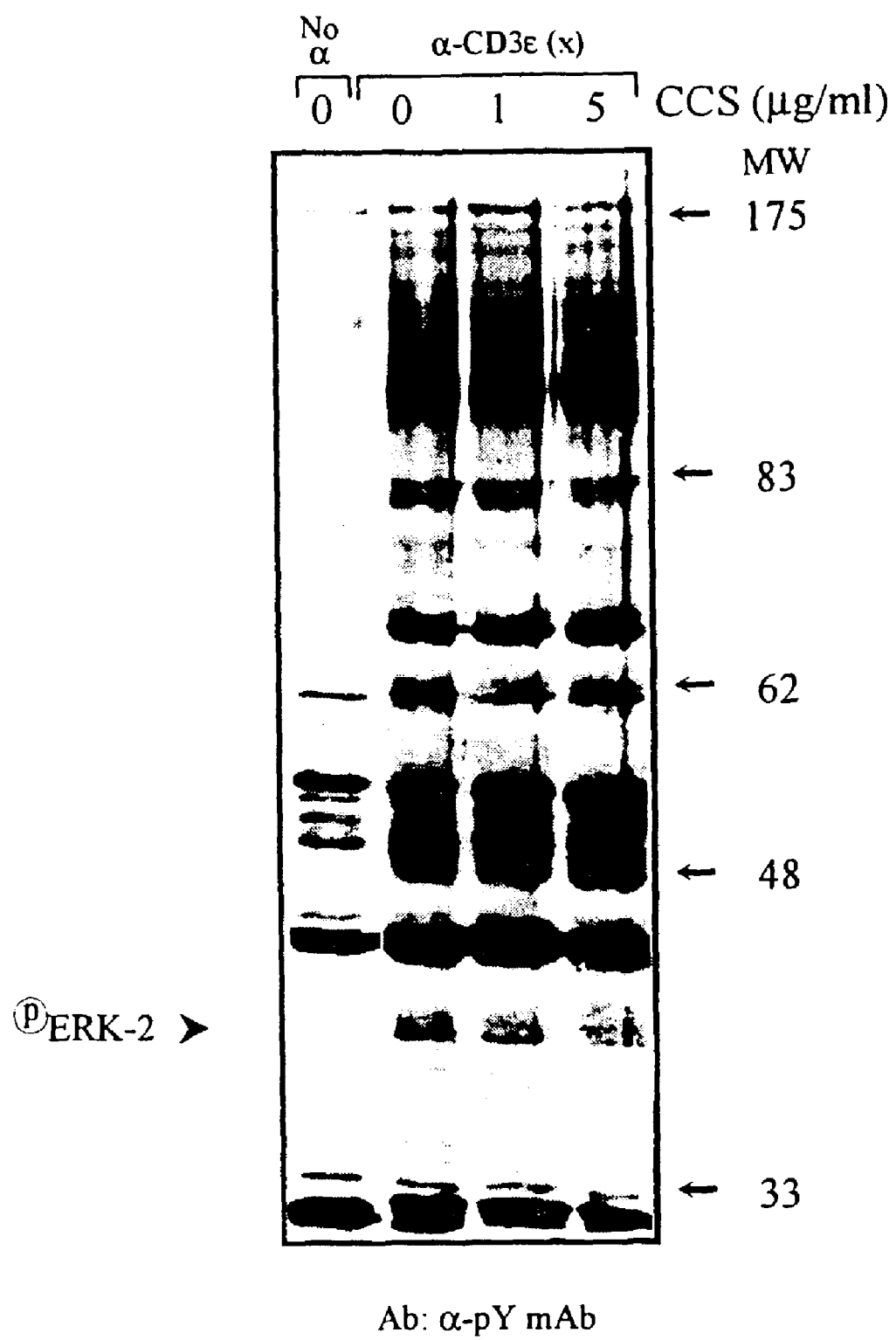

FIG. 11 is a Western blot using anti-phosphotyrosine mAb which demonstrates that CCS inhibits tyrosine phosphorylation in TCR-stimulated T cells. Th0 cells were treated with CCS (0 to 5 μg/ml) for 30 min, washed and then crosslinked anti-CD3ε mAb for 5 min. Cells were then lysed and postnuclear supernatants were subjected to SDS-PAGE and Western blotting. In this figure, the symbols denote anti-CD3ε mAb induced tyrosine phosphorylation of ERK-2, which is reduced by CCS.

Figure 12:
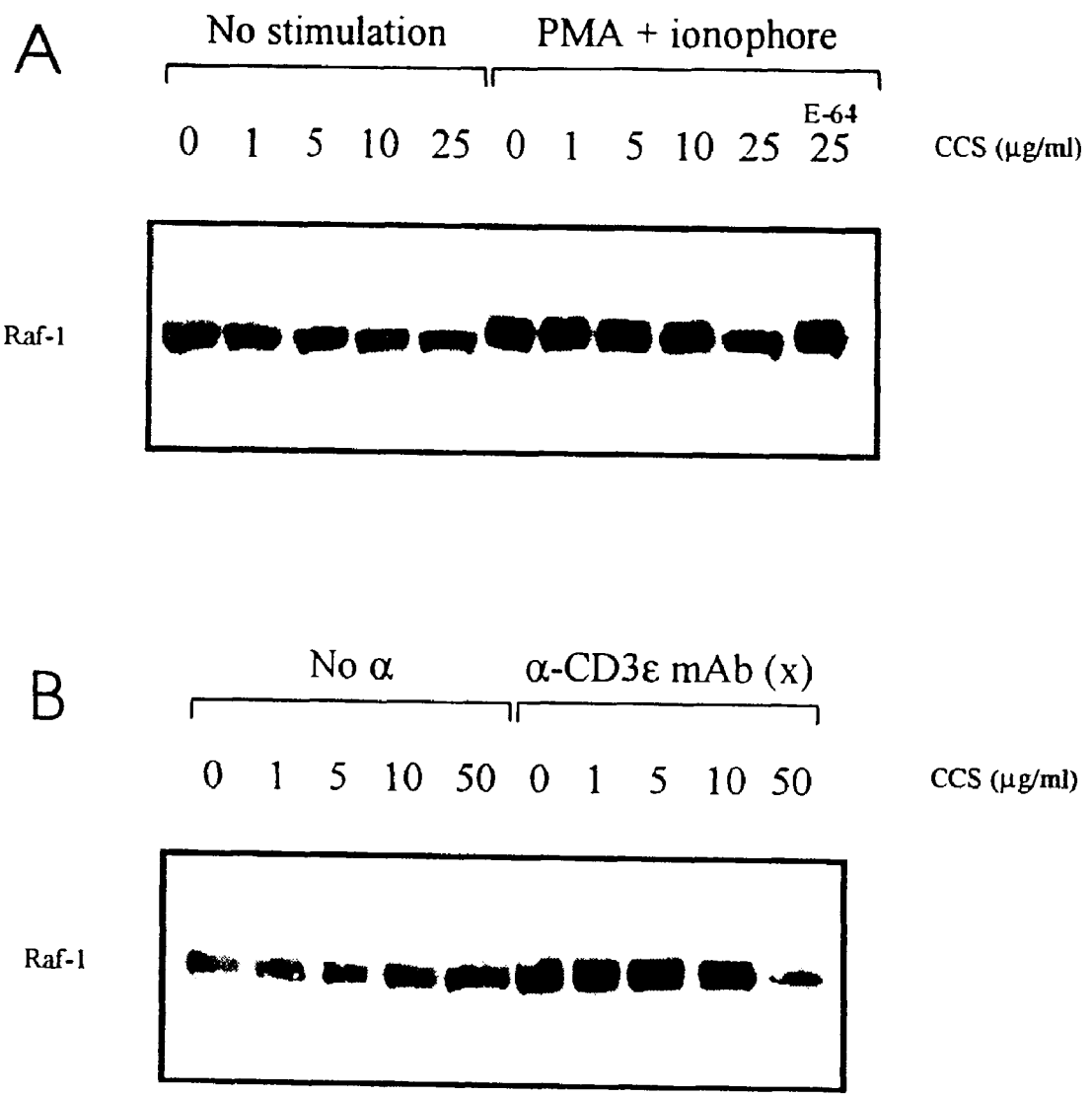

FIG. 12 is a Western blot using anti-Raf-1 mAb which shows that CCS inhibits the mobility shift of Raf-1. Th0 cells were treated with CCS (0 to 50 μg/ml) for 30 min, washed and then stimulated with either (A) combined PMA plus ionophore or (B) then crosslinked anti-CD3ε mAb for 5 min. Cells were then lysed and postnuclear supernatants were subjected to SDS-PAGE and Western blotting.

Figure 13:
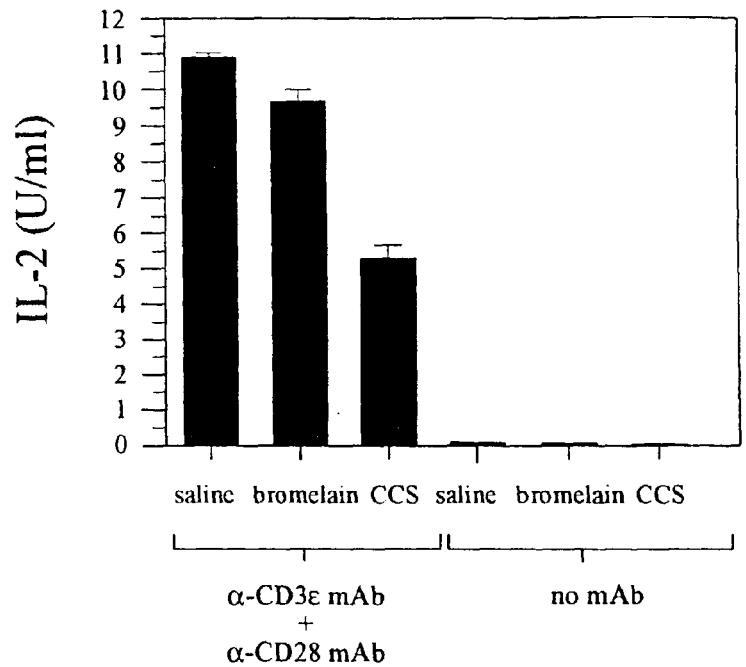
Figure 13:
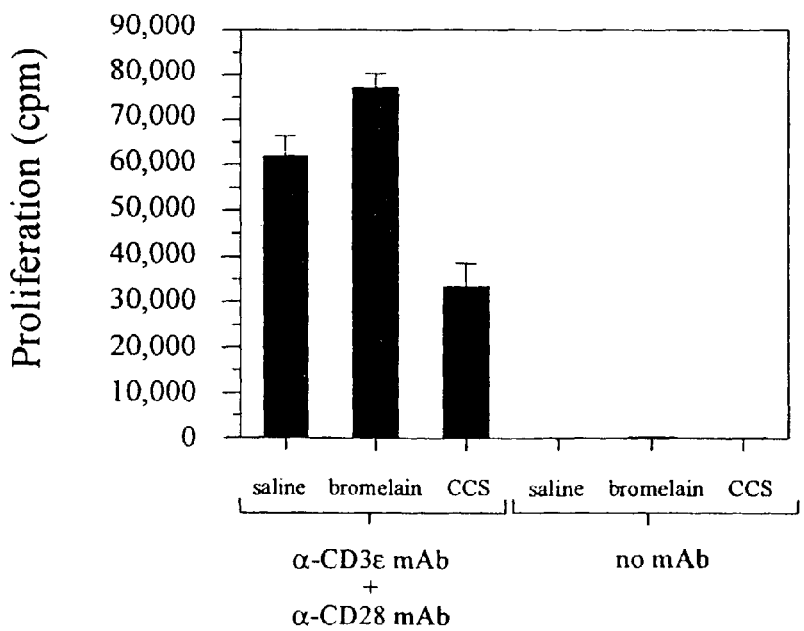

FIG. 13 is a pair of plots showing that CCS decreases IL-2 production and proliferation in purified CD4$^+$ T cells. T cells were treated with CCS (50 μg/ml), washed and then cultured in either media alone or with immobilised anti-CD3ε mAb and soluble anti-CD28 mAb. (A) IL-2 production was determined by the CTL-L assay as described in Example 5. (B) Proliferation was determined by the incorporation of $^3$H-thymidine. CD4$^+$ T cells cultured in the absence of mAb (stimuli) did not produce any detectable IL-2 and do no proliferate.

Figure 14:
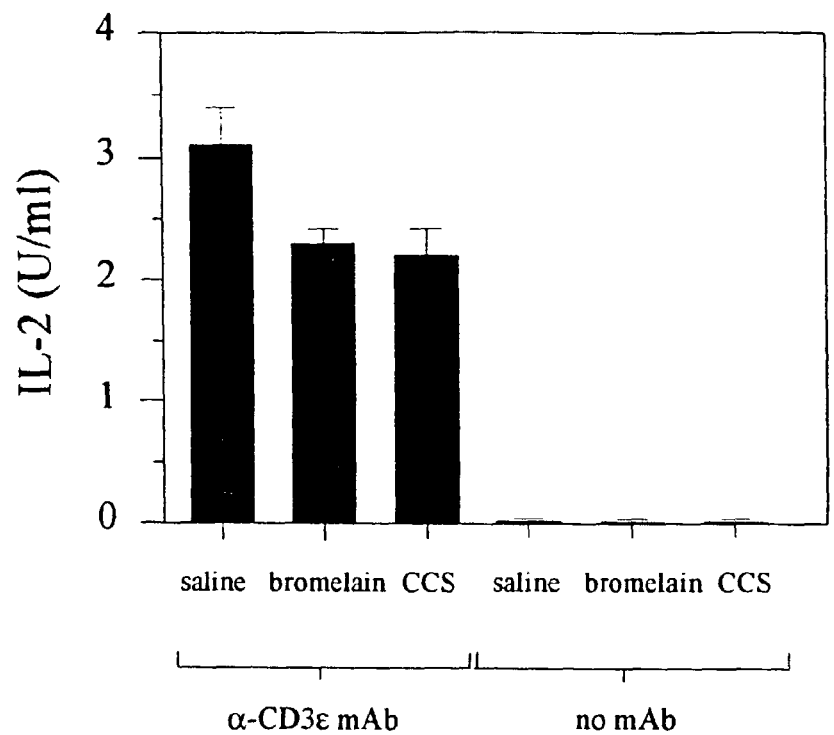
Figure 14:
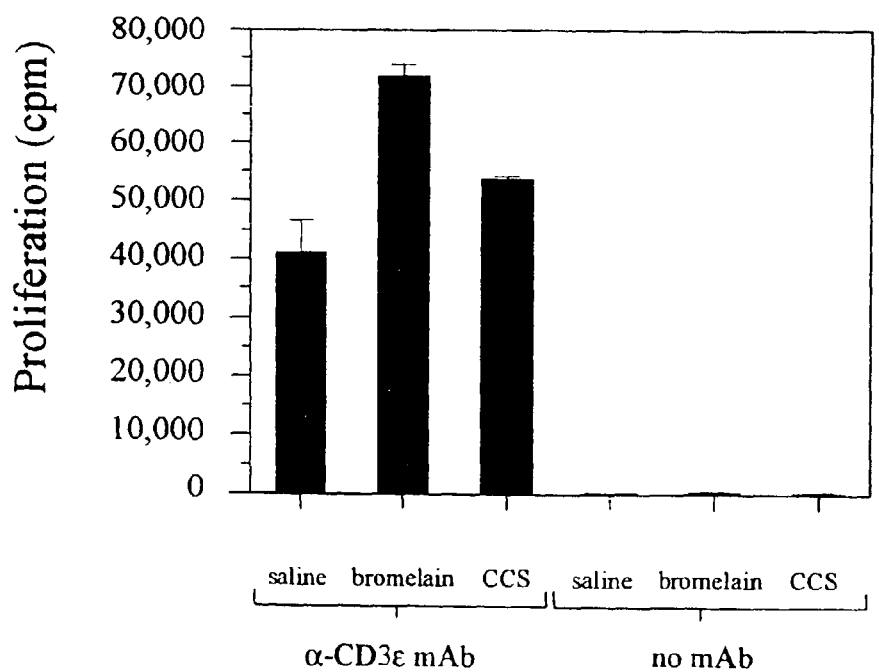

FIG. 14 is a pair of plots showing that CCS decreases IL-2 production by splenocytes but does not inhibit splenocyte proliferation. Splenocytes were treated with CCS (50 μg/ml), washed and then cultured in either media alone or with immobilised anti-CD3ε mAb. (A) IL-2 production was determined by the CTL-L assay as described in Example 5. (B) Proliferation was determined by the incorporation of $^3$H-thymidine. Splenocytes cultured in the absence of mAb (stimuli) did not produce any detectable IL-2 and do no proliferate).

Figure 15:
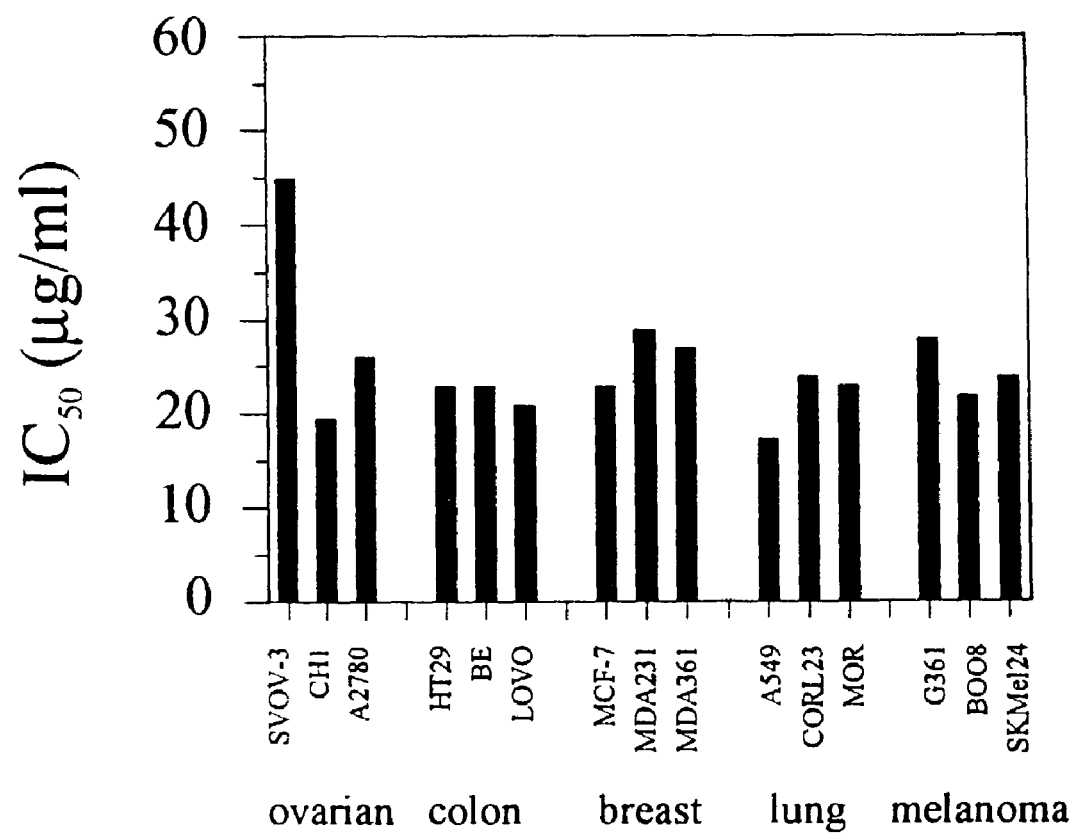

FIG. 15 is a plot which shows that CCS inhibits tumour cell growth in vitro. Cancer cell lines were treated with CCS (50, 10, 2.5, 1 and 0.25 μg/ml) or water as a control. After 96 h treatment, the effect of CCS on tumour cell growth was evaluated. Columns represent the 50% inhibitory concentrations ($IC_{50}$ μg/ml) of CCS (the amount of CCS required to inhibit 50% of tumour cell growth.

EXAMPLE 1

Purification of Bromelain Proteins a. Materials

Reagents Bromelain (E.C 3.4.22.4; proteolytic activity, 1,541 nmol/min/mg) was obtained from Solvay Inc. (Germany). Fast Flow S Sepharose, Pharmalyte 3-10™, Ampholine 9-11™, Ready Mix IEF™ (acrylamide, bisacrylamide) and IEF™ markers were obtained from Pharmacia Biotech. Precast 4-20% acrylamide gels and broad range molecular weight markers were obtained from Bio-Rad Laboratories. All other reagents were of analytical grade and obtained from either Sigma Chemical Co. or British Drug House.

b. Proteinase Assay

The proteolytic activity of bromelain was determined by use of an in-house microtitre plate based assay using the synthetic substrate Z-Arg-Arg-pNA. This assay was based on that described by Filippova et al in *Anal. Biochem.*, 143, 293-297 (1984). The substrate was Z-Arg-Arg-pNA as described by Napper et al in *Biochem. J.*, 301, 727-735, (1994).

c. Protein Assay

Protein was measured using a kit supplied by Bio-Rad that is a modified method of Lowry et al (*J. Biol. Chem.* (1951) 193, 265-275). Samples were compared to bovine serum albumin standards (0 to 1.5 mg/ml) prepared in either 0.9% saline or 20 mM acetate buffer pH 5.0, as appropriate.

d. Preparation of Bromelain

Figure 1:
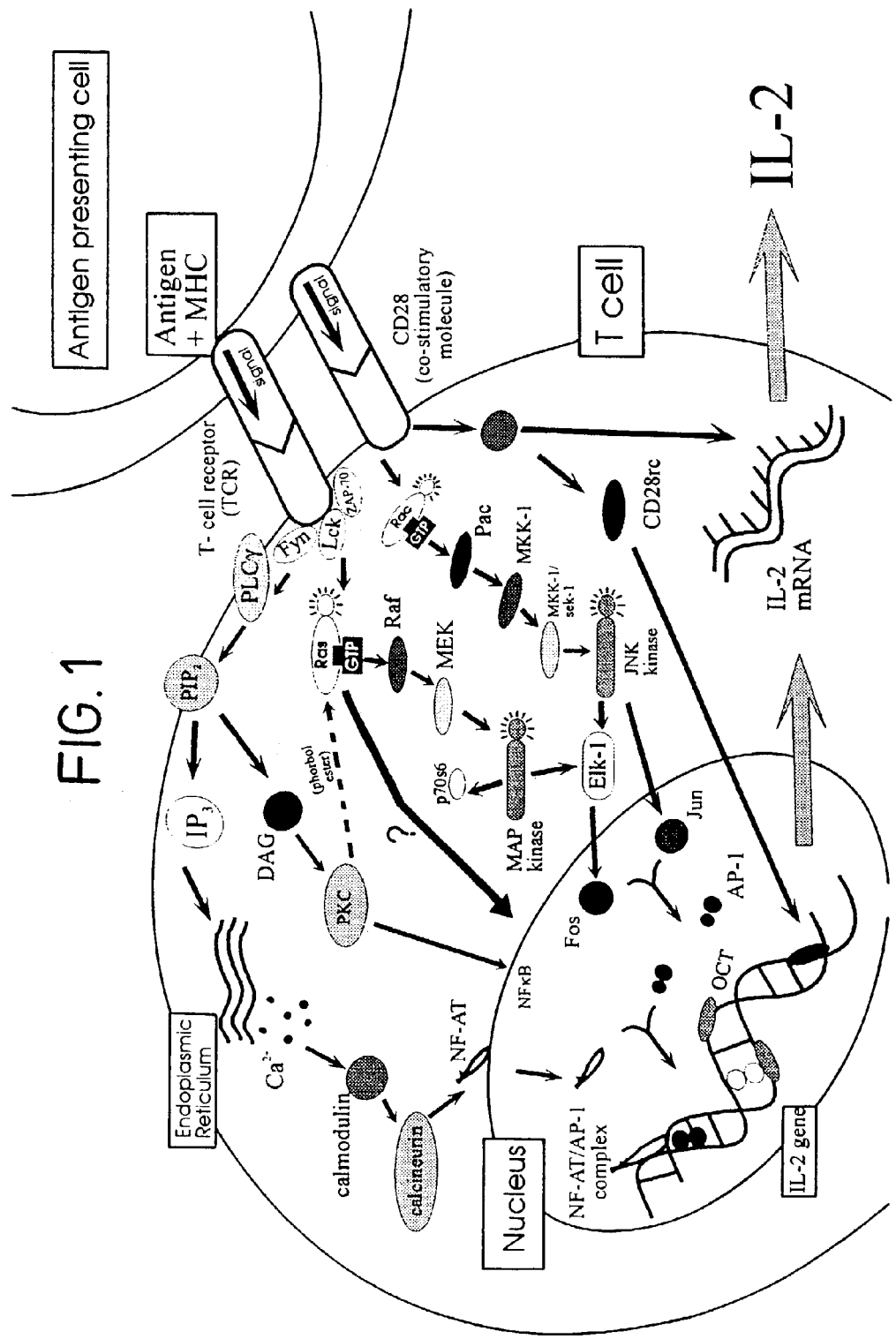
FIG. 1 is a diagrammatic representation of signal transduction events associated with T cell activation that lead to IL-2 production.
Figure 2:
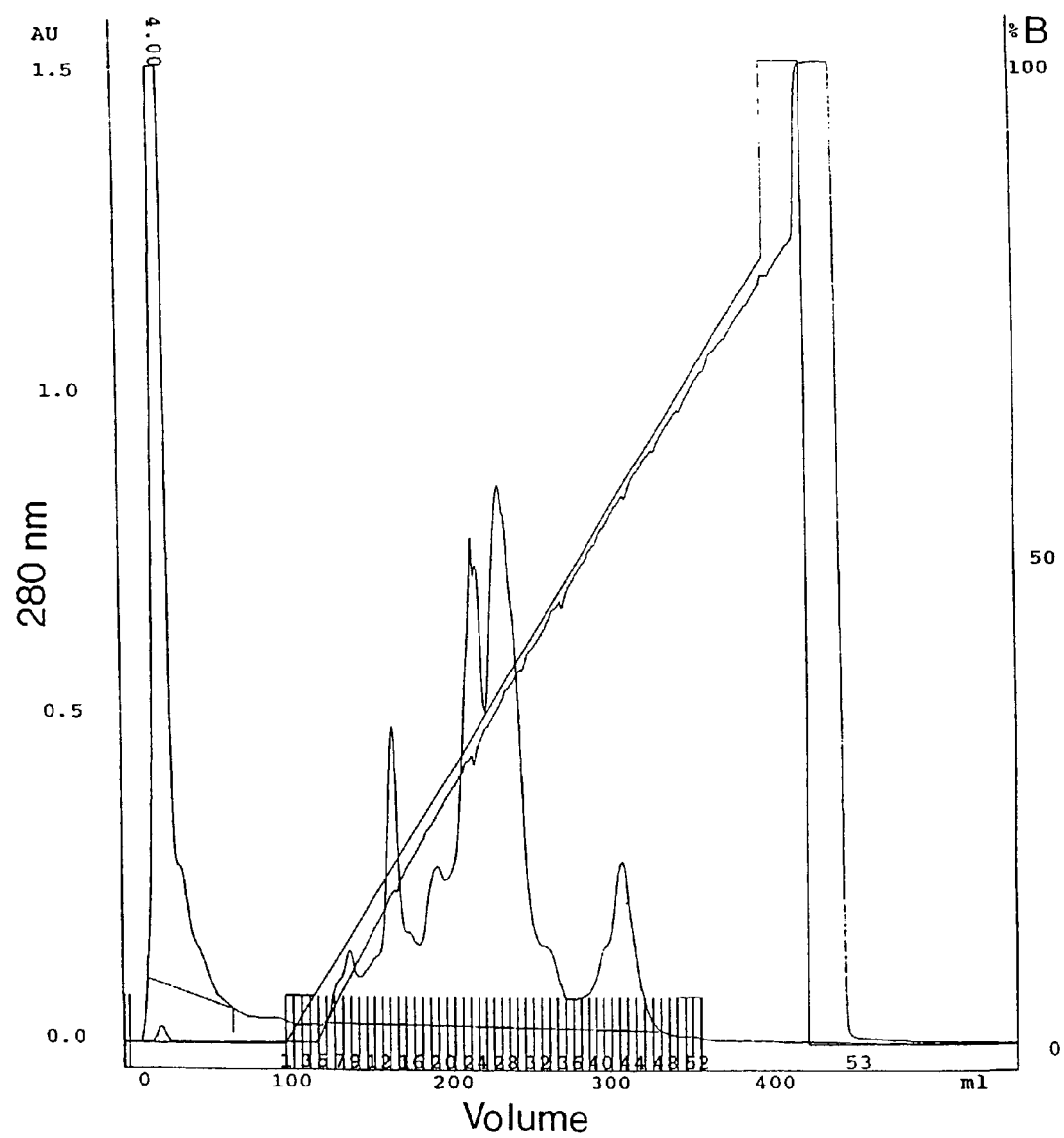
FIG. 2 is an ultra violet elution profile of crude bromelain after cation exchange chromatography on SP Sepharose high performance media.

All the following steps were performed at ambient temperature (20 to 25° C.). A solution of bromelain (30 mg/ml) was prepared by dissolving 450 mg of powder in 15 ml of 20 mM acetate buffer (pH 5.0) containing 0.1 mM EDTA, sodium. The solution was dispensed into 10×1.5 ml microcentrifuge tubes and centrifuged at 13,000×g for 10 minutes to remove insoluble material. The clear supernatants were pooled and used for chromatography e. Fast Flow S-Sepharose High Performance Chromatography A Fast flow S-sepharose column was prepared by packing 25 ml of media into an XK 16/20™ column (Pharmacia Biotech) and equilibrated with 20 mM acetate buffer (pH 5.0) containing 0.1 mM EDTA on an FPLC™ system at 3 ml/min. 5 ml of bromelain solution was injected onto the column. Unbound protein was collected and the column washed with 100 ml of acetate buffer. Protein bound to the column was eluted with a linear gradient of 0 to 0.8 M NaCl in acetate buffer over 300 ml. 5 ml fractions were collected throughout the gradient and FIG. 2 shows a typical U.V. chromatogram of crude bromelain obtained from this procedure.

Figure 3:
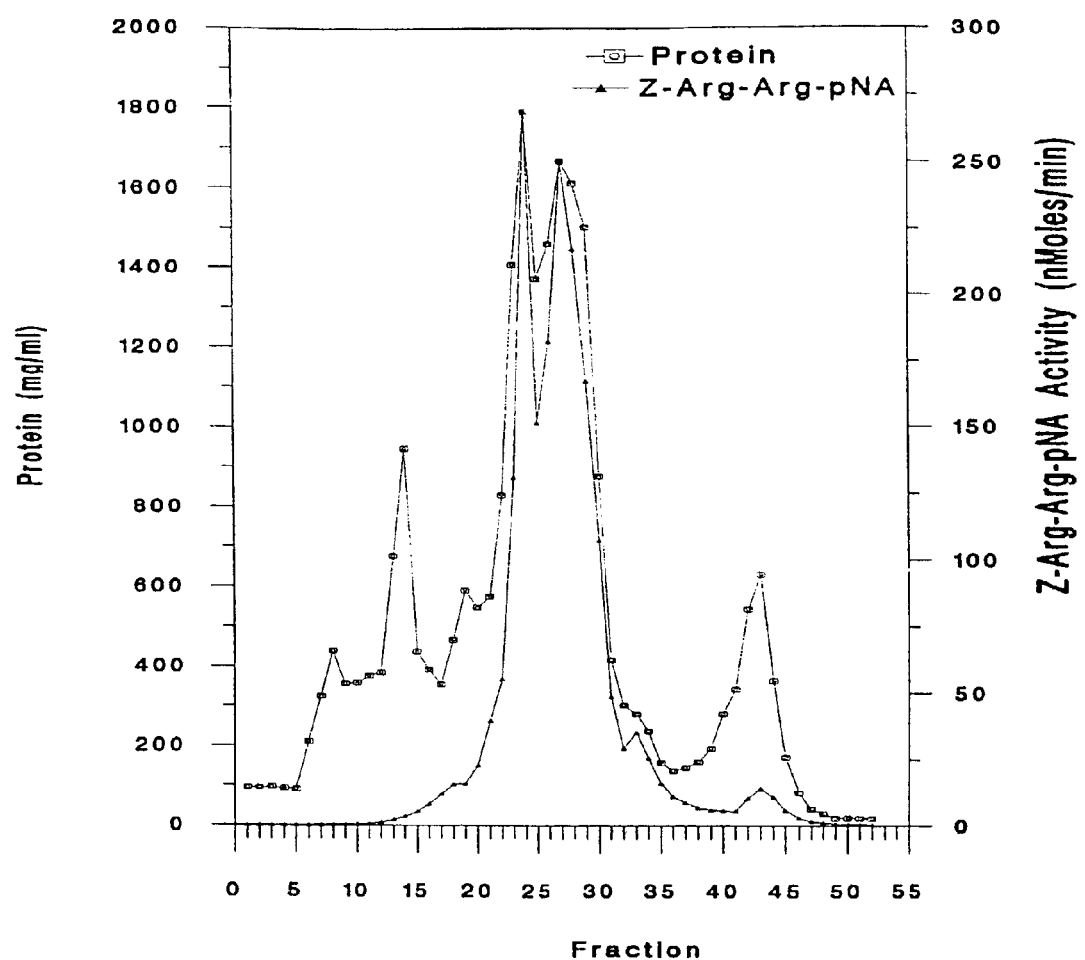
FIG. 3 is a plot showing the proteolytic activity and the protein content of crude bromelain fractions after cation exchange chromatography on SP Sepharose high performance media.

The fractions were then analysed for protein and proteolytic activity as described above and FIG. 3 shows the proteolytic activity against the synthetic peptide Z-Arg-Arg-pNA and the protein content of the individual fractions. The protein content profile closely mirrors that of the U.V., as expected, but the main proteolytic activity is confined to the two major peaks that correspond to that of bromelain protease (SBP). Small activities are observed in other areas of the chromatogram that may corresponds to other proteases distinct from SBP, such as the later eluting CCS fraction, which contains ananain and comosain.

The main peaks identified from the U.V. profile were pooled from three successive runs and named as indicated in Table 1. Pooled fractions were used for physicochemical characterisation. Pooled fractions were concentrated by ultrafiltration and buffer exchanged using PD10 columns into isotonic saline (0.9% w/v NaCl). The protein content and Z-Arg-Arg-pNA activity were calculated prior to biological testing and are shown in Table 2.

The pooled fractions were processed for analysis as described below.

TABLE 1

Summary of Pooled Fractions from SP Sepharose HP Fractionated Bromelain (QC2322)

| Component | Description | Fractions Pooled (Inclusive) |
|---|---|---|
| CCT | Flow through (unbound components) | Unbound column flow through |
| CCV | First peak off column | 8–9 |
| CCX | Second sharp peak off column | 13–14 |
| CCZ | Small peak on ascending edge of the third main bromelain peak | 19–20 |
| CCY | First main bromelain peak | 23–24 |
| CCW | Second main bromelain peak | 27–29 |
| CCU | Small peak on descending edge of the second main bromelain peak | 33–34 |
| CCS | Last double peak off column | 39–44 |

TABLE 2

Calculated Protein Content and Z-Arg-Arg-pNA Activity of Pooled Fractions used for Testing Biological Activity.

| Pooled Fractions | Z-Arg-Arg-pNA Activity (μMoles/min/ml) | Protein Content (mg/ml) |
|---|---|---|
| CCT | 11.30 | 1.00 |
| CCV | 9.78 | 1.00 |
| CCX | 71.71 | 1.00 |
| CCZ | 688.81 | 1.00 |
| CCY | 1500.0 | 0.574 |
| CCW | 1500.0 | 0.543 |
| CCU | 1500.0 | 0.421 |
| CCS | 379.76 | 1.00 | f. Processing of Pooled Fractions

The proteolytic activity and protein content of pooled fractions were determined and the concentrations adjusted to approximately either 1.4 mg/ml of protein or 105 nmoles/min/ml of proteinase activity using a Filtron™ stirred cell containing an ultrafiltration membrane of nominal molecular weight cut-off of 10 kDa. The fractions were then buffer exchanged using PD10™ columns (Pharmacia Biotech) into isotonic saline (0.9% w/v NaCl), sterile filtered (0.2 μm) and adjusted for protein content or proteolytic activity. Samples were then frozen at −80° C. and used in the in vitro studies described below.

g. Sodium Dodecyl Sulphate Polyacrylamide Gel Electrophoresis (SDS-PAGE)

Pooled FPLC™ samples were analysed by sodium dodecyl sulphate polyacrylamide gel electrophoresis (SDS-PAGE) on precast 4 to 20% T gradient gels. Samples were prepared for electrophoresis by acid precipitation in which 100 μl was mixed with an equal volume of 20% w/v tricloroacetic acid (TCA). Precipitated protein was collected by centrifugation at 13,000×g for 10 minutes and the supernatant discarded. The pellet was washed twice with 0.5 ml of diethyl ether and left to dry in air at ambient temperature. The pellets were then dissolved in 300 μl of SDS-PAGE sample buffer (62.5 mM Tris-HCl pH 6.8 containing 10% v/v glycerol, 2% w/v sodium dodecyl sulphate and 40 mM dithiothreitol) and heated at 95° C. in a water bath.

SDS-PAGE broad range molecular weight standards diluted 1:20 in SDS-PAGE sample buffer were treated similarly and run with the samples. Gels were run on a mini Protean II™ electrophoresis system according to Bio-Rad's protocol at 240 V and until the dye front reached the end of the gel (30 to 45 min).

After electrophoresis, separated proteins were stained overnight with orbital mixing in a solution of 0.075% w/v colloidal brilliant blue G-250 containing 1.5% v/v phosphoric acid, 11.25% w/v ammonium sulphate and 25% v/v methanol. Gels were destained, to obtain a clear background, in a solution of 25% v/v methanol and 10% v/v acetic acid.

Results

The purity of fractions is shown by SDS-PAGE in FIG. 4. All of the pooled fractions except the column flow through (CCT) showed that the major protein present was of molecular weight between approximately 25-28 kDa. This corresponds to the molecular weight of cysteine proteinases isolated from bromelain by other authors (Rowan et al, *Methods in Enzymology*, (1994), 244, 555-568). The purity of fractions CCX, CCZ, CCY and CCW appears to be high. Minor components of lower molecular weight can be observed in some fractions, particularly CCT, CCV, CCX and CCS. Pooled fractions CCU and CCS contain a doublet between 25-28 kDa; the higher gel loadings of fractions CCX, CCZ, CCY, and CCW means that doublet bands may also be present in these fractions. A summary of the components and their calculated molecular weights in pooled fractions, as determined by SDS-PAGE, is shown in Table 3.

Proteins in pooled fractions CCX, CCZ, CCY+CCW and CCU were transferred onto nitro-cellulose after SDS-PAGE by Western blotting and probed with rabbit antisera raised against purified stem bromelain protease (SBP) (results not shown). All protein bands in these pooled fractions were recognised by antibodies in the sera, indicating immunologically similar proteins, probably belonging to the cysteine proteinase family of enzymes.

TABLE 3

Summary of the Molecular Weights of Proteins found in SP Sepharose LIP Pooled Fractions as Determined by SDS-PAGE.

| Pooled Fractions | Molecular Weight (kDa) of Major Protein Band(s) | Molecular Weight (kDa) of Minor Protein Band(s) |
|---|---|---|
| CCT | 76.03 | 15.07 |
| CCV | 15.07, 25.85, 28.28, 76.03 | |
| CCX | 25.08 | 15.07, 76.03 |
| CCZ | 27.45 | 13.37, 16.49, 76.03 |
| CCY | 27.45 | 6.5 |
| CCW | 27.45 | |
| CCU | 27.45, 28.28 | |
| CCS | 15.07, 25.85, 27.45 | | h. Isoelectric Focusing

Pooled fractions (0.5 to 1.0 mg/ml) were diluted 1:3 with deionised water and run on gradient gels of pH 3 to 11. Gels were cast using Ready Mix IEF™ to produce a 5.5% T, 3% C polyacrylamide gel containing 10% v/v glycerol, 5.0% Pharmalyte 3-10™ and 2.5% Ampholine 9-11™. Briefly, 10 μl of sample and high PI markers were loaded onto the gel after prefocusing at 700 V. Sample entry was at 500 V for 10 min, focusing was at 2500 V for 1.5 hour and band sharpening at 3000 V for 10 min. After electrophoresis the proteins were fixed with a solution of 20% w/v TCA for 30 min, washed in destain for 30 min to remove TCA and stained with brilliant blue G-250 as described for SDS-PAGE (see above).

Results

FIG. 5 shows that all fractions except CCX contained basic proteins focusing beyond the 9.3 pI marker. Localised charge interactions with the chromatographic media functional groups may explain why proteins of pI 3.8 and 3.85 in CCX, adsorbed onto a cation exchange resin at pH 5.0. CCZ was present as a single band of pI 9.7, whilst pooled fractions CCY, CCW, and CCU contained multiple bands of isoelectric points in the range pH 9.5-9.8. At least part of this heterogeneity can be explained by variation in the carbohydrate moiety of a common stem bromelain protein backbone. The values are in agreement with those reported in the literature of pI 9.45-9.55 for bromelain (Rowan et al, *Methods in Enzymology*, (1994), 244, 555-568). Pooled fractions CCS contains two basic proteins of pI greater than 10.25. Estimates by extrapolation give pIs of 10.4 and 10.45. These correspond to ananain and comosain, and arc in agreement with other estimates (Rowan et al, as above) of pIs greater than 10. The pIs of proteins in each of the pooled fractions are summarised in Table 4.

TABLE 4

Summary of the estimated Isoelectric points of Proteins found in SP Sepharose HP Pooled Fractions.

| Pooled Fractions | Isoelectric Points of Proteins |
|---|---|
| CCT | Not detected |
| CCV | Not Detected |
| CCX | 3.8, 3.85 |
| CCZ | 9.7 |
| CCY | 9.6, 9.7 |
| CCW | 9.57, 9.6, 9.7 |
| CCU | 9.57, 9.6, 9.75 |
| CCS | 10.4, 10.45 |

EXAMPLE 2

NH$_2$-terminal Amino Acid Analysis of Bromelain Components

In a separate experiment, pooled fractions of bromelain were run by SDS PAGE and blotted as above onto PVDF membrane. The membrane was stained with 0.025% w/v coomassie blue R-250, dissolved in 40% v/v methanol for 10 min. followed by destaining in 50% v/v/methanol. The membrane was dried in air at room temperature and NH$_2$-terminal amino acid sequencing of the stained proteins was carried out. Briefly, the protein band was cut from the membrane and placed in the upper cartridge of the sequencer. NH$_2$-terminal amino acid analysis of bromelain components was determined by Edman degradation using a gas phase sequencer (Applied Biosystems), equipped with an on-line phenylthiohydantion amino acid analyser. Table 5 shows the first NH$_2$-terminal amino acids of CCZ (SEQ ID NO: 1), CCX (SEQ ID NO: 2), stem bromelain protease (SEQ ID NO: 3), ananain (SEQ ID NO: 4) and comosain (SEQ ID NO: 5).

Table 5. NH$_2$-Terminal Sequence Similarities of CCZ Protein and Those of Known Proteinases Isolated form Bromelain.

TABLE 5

NH$_2$-Terminal Sequence Similarities of CCZ Protein and Those of Known Proteinases Isolated from Bromelain.

| Proteinase | Position from N-Terminus |
|---|---|
| CCZ | VLPDSIDWRQKGAVTEVKNRG<br>1    5    10    15    20 |
| CCX | VPQSIDWRDYGAVNEVKN<br>4    9    14 |

TABLE 5-continued

NH$_2$-Terminal Sequence Similarities of CCZ Protein and Those of Known Proteinases Isolated from Bromelain.

| Proteinase | Position from N-Terminus |
|---|---|
| Stem Bromelain Protease | AVPQSIDWRDYGAVTSVKNQN<br>1    5    10   15   20 |
| Ananain | VPQSIDWRDSGAVTSVKNQG<br>1  4    9    14   19 |
| Comosain | VPQSIDWRNYGAVTSVKNQG<br>1  4    9    14   19 |

All proteins share sequence homologies. Ananain and comosain differ by 2 out of 20 amino acids when compared to stem bromelain protease. CCZ differs by 8 out of 21 amino acids when compared to stem bromelain protease. CCZ differs from ananain and comosain by 6 out of 20 amino acids. Comosain differs by 2 amino acids from ananain. Whilst it is clear that these proteins are structurally related, they are all distinct, showing divergence from each other. These proteinases also differ in their proteinase substrate specificity and their biological activity.

EXAMPLE 3

Fraction CCS Inhibits Tyrosine Phosphorylation of p42 kda Phosphoprotein.

a. Materials

Antibodies Anti-CD3 ε-chain mAb (145-2C11) and anti-CD28 mAb (PV-1) were purchased from Pharmingen (San Diego, Calif.) and goat anti-hamster IgG Ab was from Sigma (Dorset, UK). Mouse anti-phosphotyrosine mAb (4G10), mouse anti-MAPk R2 (ERK-2) mAb and mouse anti-Raf-1 mAb were from UBI (Lake Placid, N.Y.). Goat anti-mouse and goat anti-rabbit IgG Ab conjugated to horse radish peroxidase (HRP) were from BioRad (Hemel Hemstead, Hertfordshire, UK). Rabbit polyclonal phospho-specific MAPk IgG which recognise tyrosine phosphorylated p44 and p42 MAPks were from New England BioLabs (Hitchin, Hertfordshire, UK).

Reagents Phorbol 12-myristate 13-acetate (PMA) and calcium ionophore A23187 were purchased from Sigma. Bromelain (E.C 3.4.22.4; proteolytic activity, 1,541 nmol/min/mg) was obtained from Solvay Inc. (Germany). E-64 (L-transepoxysuccinylleucylamido-(4-guanidino)butane, a selective cysteine protease inhibitor, was from Sigma.

Cells The T cell hybridoma GA15 was a generous gift from B. Fox (ImmuLogic Pharmaceutical Corporation, Boston, Mass.). GA15 was generated by fusing the thymoma BW5147 with the T$_h$2 clone F4 specific for KLH in association with I-A$^b$, and were maintained as previously described (Fox, 1993, *Int. Immunol.*, 5, 323-330). GA15 exhibit a T$_h$0 cell phenotype as they produce IL-2, IL-4 and IFN-γ following stimulation with crosslinked anti-CD3ε mAb (Fox, 1993).

b. Stimulation of T cells. Cells ($2 \times 10^7$) suspended in RPMI 1640 were treated with CCS (1 to 50 μg/ml) diluted in saline (0.9% (w/v)) for 30 min at 37° C. Mock treated cells were treated with an equal volume of saline (diluent). At high concentrations of CCS (50 or 100 μg/ml) cell aggregation occurred, as noted previously in studies with crude bromelain. Following treatment, cell aggregates were gently dispersed by washing cells 3 times and then resuspending in fresh RPMI. Cells were stimulated via the cell surface with crosslinked mAb to the TCR (anti-CD3ε), or directly, using combined PMA (20 ng/ml) and ionophore (1 μM) for times indicated in figure legends and the text.

Stimulation via the TCR was conducted by first incubating T cells on ice for 30 min with anti-CD3ε mAb (20 μg/ml). Excess mAb was then removed by washing once at 4° C. and anti-CD3ε mAb was crosslinked with goat anti-hamster IgG (20 μg/ml) at 37° C. Stimulation was terminated by the addition of ice-cold lysis buffer (25 mM Tris, pH 7.4, 75 mM NaCl, 2 mM EDTA, 0.5% Triton X-100, 2 mM sodium orthovanadate, 10 mM sodium fluoride, 10 mM sodium pyrophosphate, 74 μg/ml leupeptin, 740 μM PMSF and 74 μg/ml aprotinin) for 30 min with continual rotation at 4° C. Lysates were clarified (14,000×g for 10 min) and an equal volume of 2×SDS-PAGE sample buffer (50 mM Tris, pH 7, 700 mM 2-ME, 50% (v/v) glycerol, 2% (w/v) SDS, 0.01% (w/v) bromophenol blue) was added to postnuclear supernatants. Proteins were solubilised at 100° C. for 5 min and samples containing $1 \times 10^6$ cell equivalents were resolved by SDS-PAGE.

c. Immunoblotting. Separated proteins were transferred to nitrocellulose membranes (Bio-Rad) which were then blocked with 5% (w/v) bovine serum albumin (Sigma, fraction V; BSA), 0.1% Nonidet p-40™ in Tris-buffered saline (170 mM NaCl and 50 mM Tris, pH 7.4; TBS). Immunoblots were incubated with the appropriate antibodies as indicated in figure legends. Primary antibodies were diluted in antibody dilution buffer comprised of 0.5% (w/v) BSA, 0.1% (v/v) Tween-20 in TBS at 4° C. for 2 h followed by detection with the appropriate secondary antibody conjugated to horseradish peroxidase diluted in antibody dilution buffer at 4° C. for 1 h. Following each incubation step, membranes were washed extensively with 0.1% Tween-20 in TBS. Immunoreactivity was determined using the ECL chemiluminescence detection system (Amersham Corp., Arlington Heights, Ill.).

d. Inhibition of proteolytic activity of CCS. A specific cysteine protease inhibitor, E-64, was used to inactivate the proteolytic activity of CCS. CCS (25 μg/ml) diluted in 3 μM dithiothreitol, 100 μM E-64, 60 mM sodium acetate (pH 5) was incubated for 10 minutes at 30° C. The inactivated CCS was then dialysed overnight in saline at 4° C. Earlier studies with crude bromelain have shown that these conditions are sufficient to induce 99.5% inactivation of proteolytic activity as assayed with the Z-Arg-Arg-pNA substrate (see above). T cells were treated with E-64 inactivated CCS (25 μg/ml) and compared with untreated CCS and mock-treated T cells stimulated with PMA plus ionophore.

Results a. Fraction CCS inhibits tyrosine phosphorylation of p42 kda phosphoprotein. We have previously shown that bromelain blocks tyrosine phosphorylation of ERK-2 following stimulation of T cells with combined PMA plus calcium ionophore (WO-A-96/00082). Phorbol ester and ionophore stimulation of T cells act synergistically to reproduce many features of TCR stimulation such as IL-2 secretion, IL-2 receptor expression, and T cell proliferation (Truneh et al., 1985, *Nature*, 313, 318-320; Rayter et al., 1992, *EMBO*, 11, 4549-4556). Phorbol esters can mimic antigen receptor triggering and bypass TCR-induced protein tyrosine kinases to activate ERK-2 by a direct agonist action on PKC and p21$^{RaS}$. Calcium ionophore A23187 induces increased intracellular release of $Ca^{2+}$ and therefore mimics the action of inositol 1,4,5-trisphosphate ($IP_3$). Phorbol esters and ionophore however, stimulate PKC pathways that are not controlled by the TCR (Izquierdo et al., 1992, *Mol. Cell. Biol.*, 12, 3305-3312) suggesting separate intracellular pathways within T cells that regulate T cell function. We therefore investigated which fraction of bromelain could block T cell signalling via the TCR-independent pathway by examining its effect on PMA and ionophore-induced tyrosine phosphorylation.

Stimulation of T cells with combined ionophore and PMA induced tyrosine phosphorylation of several proteins including those of circa 100 kda, 85 kda, 42 kda and 38 kda. CCS (50 µg/ml) pre-treatment reduced tyrosine phosphorylation of the p42 kda protein, and did not significantly inhibit phosphorylation of any other substrate (FIG. 6). In two experiments, CCS, but no other fraction, also increased tyrosine phosphorylation of circa 36 kda, 38 kda, 85 kda, 94 kda and 102 kda proteins (FIG. 7 and FIG. 8).

The ability of CCS to block tyrosine phosphorylation of the 42 kda phosphoprotein was dose-dependent (FIG. 8) and dependent on its proteolytic activity, since E-64 completely abrogated the inhibitory effect of CCS on p42 kda phosphorylation (FIG. 8). E-64 treatment of T cells did not affect PMA and ionophore-induced T cell signalling.

CCS inhibits ERK-2 tyrosine phosphorylation. We suspected that the 42 kda phosphoprotein inhibited by CCS was the MAPk ERK-2, so we conducted immunoblot analysis with specific anti-ERK-2 mAb and anti-phospho MAPk antibodies, which specifically detects ERK-1 and ERK-2 only when catalytically activated by phosphorylation at Tyr204. Immunoblotting of CCS-treated cells that had been stimulated with PMA plus ionophore, confirmed that the p42 kda phosphoprotein was indeed ERK-2 (FIG. 9).

CCS reduces TCR-induced tyrosine phosphorylation of ERK. We next investigated the effect of CCS on TCR-mediated signal transduction by assessing substrate tyrosine phosphorylation of GA15 stimulated with crosslinked anti-CD3ε mAb. Immunoblots of GA15 lysates, using specific anti-phosphotyrosine mAb, revealed increased tyrosine phosphorylation of multiple proteins including those of circa 120 kda, 100 kda, 85 kda, 76 kda, 70 kda, 42 kda and 40 kda, consistent with phosphoproteins observed in other T cell lines following TCR-ligation (June et al, 1990, *J. Immunol.*, 144, 1591-1599 and *Proc. Natl. Acad. Sci. USA*, 87, 7722-7726, reviewed by Cantrell, 1996, *Annu. Rev. Immunol.*, 14, 259-274) (FIG. 10). Tyrosine phosphorylated proteins were readily detected between 2 and 5 min following stimulation and remained phosphorylated for at least 10 min (FIG. 10). GA15 cells stimulated with anti-CD3 mAb alone or cross-linking Ab, did not induce tyrosine phosphorylation of any cellular substrate (data not shown). Again, CCS pretreatment of GA15 for 30 min caused a reduction in TCR-induced protein tyrosine phosphorylation of ERK-2 in a dose-dependent manner (FIG. 11). CCS did not markedly affect tyrosine phosphorylation of other TCR-induced phosphoproteins, suggesting that CCS has a selective mode of action.

EXAMPLE 4

CCS Retards the Mobility Shift of Raf-1

Raf-1 is an immediate upstream activator of MEK-1 which activates ERK-2. Raf-1 activation requires phosphorylation on specific serine and threonine residues (Avruch et al., 1994, *TIBS*, 19, 279-283). To investigate whether CCS affects any other substrates upstream from ERK-2 in the MAP kinase cascade, we investigated the effect of CCS on Raf-1. T cells were treated with CCS (0 to 50 µg/ml) and then stimulated with either anti-CD3ε, mAb or combined PMA plus ionophore as described earlier. Results show that CCS blocks the mobility shift of Raf-1, indicating that it blocks its protein phosphorylation and thus activation. This data confirms that CCS has an effect on the MAP kinase cascade (FIG. 12) and that the effect of CCS may not be directly on ERK-2, but on upstream substrates in the MAPk cascade.

EXAMPLE 5

Effect of CCS on IL-2 Production and T cell Proliferation a. Materials

Cells Splenocytes were isolated from female BALB/c mice (6-8 weeks old), as previously described in WO-A-96/00082. Highly purified $CD4^+$ T cells were isolated from splenocytes using magnetic activated cell sorting (MACS).

b. Interleukin 2 production. T cells diluted in RPMI were treated with CCS (50 µg/ml) or saline at 37° C. for 30 min, washed in fresh RPMI and then resuspended in culture medium. T cells were stimulated to produce cytokine mRNA by immobilised anti-CD3ε (4 µg/ml) and soluble anti-CD28 (10 µg/ml). Anti-CD3ε mAb diluted in PBS was immobilised to 24-well, flat bottom, microculture plates (Corning, Corning, N.Y.) by incubation for 16 hours at 4° C. Wells were then washed three times in PBS prior to addition of triplicate cultures of either splenocytes or purified $CD4^+$ T cells (2.5-$5 \times 10^6$ cells per well) which were incubated at 37° C. in humidified 5% $CO_2$ for 24 h. IL-2 levels in the culture supernatant were measured using the CTL-L bioassay (Gillis et al., 1978, *J. Immunol.*, 120, 2027-2032).

c. T Cell Proliferation. T cells were treated with CCS (50 µg/ml) for 30 min, washed in RPMI then stimulated with immobilised anti-CD3ε mAb alone or combined anti-CD3ε mAb plus anti-CD28 mAb. Cells were then cultured in 96 well, flat-bottom plates (Nunc) at $10^5$ cells per well for 36 h. Cultures were pulsed with 0.5 µCi of [$^3$H]TdR 12 h prior to harvesting onto glass fibre filters.

Results a. CCS inhibits IL-2 production and proliferation of $CD4^+$ T cells. Activation of $p21^{Ras}$, Raf-1, MEK-1 and ERKs are essential for induction of IL-2 transcription in T cells (Izquierdo et al., 1993, *J. Exp. Med.*, 178, 1199). IL-2 is the major autocrine T cell growth factor which induces proliferation of T cells. The defect in ERK activation demonstrated here could therefore be expected to inhibit IL-2 production and T cell proliferation. We therefore investigated whether CCS could effect a functional outcome of T cell signalling, namely IL-2 production and proliferation in murine splenocytes and highly purified $CD4^+$T cells. CCS (50 µg/ml) treatment of purified $CD4^+$T cells reduced both IL-2 production and proliferation when the ERK pathway was stimulated with anti-CD3ε mAb (FIGS. 13a and 13b). CCS also blocked IL-2 production by splenocytes, however it did not affect splenocyte proliferation (FIGS. 14a and 14b), suggesting that an as yet unidentified component in CCS was acting on accessory cell populations in splenocyte cultures, such as B cells or macrophages. Bromelain can increase costimulatory signals to T cells via an action on B cells. Regardless of the putative effect of CCS on accessory cells, data clearly indicate that CCS blocks IL-2 production and proliferation of purified $CD4^+$ T cells, suggesting that CCS blocks T cell activation. IL-2 production and proliferation were dependent on cell stimulation with anti-TCR antibodies as no cytokine was detected in cells cultured in tissue culture media alone (FIGS. 13 and 14).

EXAMPLE 6

Effect of CCS on Human Tumour Cell Growth In Vitro a. Materials

Cells Tumour cell lines were provided by L. Kelland (Institute of Cancer Research, Sutton, UK) and were as follows; ovarian (SKOV-3, CH-1, A2780), colon (HT29, BE, LOVO), breast (MCF-7, MDA231, MDA361), lung (A549, CORL23, MOR) and melanoma (G361, B008, SKMe124).

b. Growth Inhibition of Human Tumour Cell Lines. Studies were conducted by L. Kelland (Institute of Cancer Research, Sutton, UK). Cell lines were trypsinised and single viable cells were seeded into 96-well microtitre plates at a density of $4\times10^3$ cells/well in 160 µl growth medium. After allowing for attachment overnight, CCS was then added to quadruplicate wells in 40 µl of growth medium to give a range of final concentrations in wells of 50, 10, 2.5, 1 and 0.25 µg/ml. Eight wells served as control, untreated wells. CCS was diluted immediately prior to addition to cells in sterile water. CCS exposure to cells was for 96 h whereupon the cell number in each well was determined by staining with 0.4% sulforhodamine B in 1% acetic acid as described previously (Kelland et al., 1993, *Cancer Res.*, 53, 2581-2586). 50% inhibitory concentrations ($IC_{50}$ values in µg/ml) were then calculated from plots of concentration versus control (%) absorbance (read at $540_{nm}$).

Results a. CCS inhibits human tumour growth in vitro. $p21^{Ras}$ and Raf-1 are important oncogenes, which when mutated cause uncontrolled cell growth and proliferation, leading to cancer. Since we have shown that CCS can block the effects of the $p21^{Ras}$/Raf-1/MEK1/ERK kinase signalling cascade, we investigated whether CCS could block tumour growth. CCS treatment of human tumour cells resulted in a reduction in the growth of several different ovarian, lung, colon, breast and melanoma tumour cell lines in vitro (FIG. 15). CCS did not affect all cell lines equally, suggesting that CCS has a selective action.

---

The invention claimed is:

1. A method for the treatment of an inflammatory disease or an inflammatory condition in a patient in need of such treatment, said method comprising either enteral or parenteral administration to said patient of an effective amount of an agent, wherein said agent is a component of bromelain comprising proteins having molecular weights of about 15.07 kDa, 25.85 kDa, and 27.45 kDa as determined by SDS-PAGE and having isoelectric points of 10.4 and 10.45, wherein said component of bromelain does not comprise a protein comprising an N-terminal amino acid sequence of SEQ ID NO: 1 and having an isoelectric point of 9.7, and wherein said component of bromelain is obtainable by a method comprising:

(i) dissolving bromelain in acetate buffer at pH 5.0,
(ii) separating the components of the bromelain by fast flow high performance liquid chromatography on S-sepharose eluted with a linear gradient of 0 to 0.8 M sodium chloride in acetate buffer over 300 ml,
(iii) collecting the fraction corresponding to a final double peak off the column, and
(iv) isolating proteins from the fraction collected in (iii), whereby a protein comprising an N-terminal amino acid sequence of SEQ ID NO: 1 and having an isoelectric point of 9.7 is absent from said component of bromelain, to thereby inhibit or suppress T cell activation in said patient, such that said inflammatory disease or inflammatory condition in said patient is treated.

2. The method of claim 1, wherein inhibition or suppression of T cell activation is through inhibition of a mitogen-activated protein kinase pathway.

* * * * *

SEQUENCE LISTING

<160> NUMBER OF SEQ ID NOS: 5

<210> SEQ ID NO 1
<211> LENGTH: 21
<212> TYPE: PRT
<213> ORGANISM: Ananas comosus

<400> SEQUENCE: 1

Val Leu Pro Asp Ser Ile Asp Trp Arg Gln Lys Gly Ala Val Thr Glu
1               5                   10                  15

Val Lys Asn Arg Gly
            20

<210> SEQ ID NO 2
<211> LENGTH: 18
<212> TYPE: PRT
<213> ORGANISM: Ananas comosus

<400> SEQUENCE: 2

Val Pro Gln Ser Ile Asp Trp Arg Asp Tyr Gly Ala Val Asn Glu
1               5                   10                  15

Val Lys Asn

<210> SEQ ID NO 3
<211> LENGTH: 21
<212> TYPE: PRT
<213> ORGANISM: Ananas comosus

<400> SEQUENCE: 3

Ala Val Pro Gln Ser Ile Asp Trp Arg Asp Tyr Gly Ala Val Thr Ser
1               5                   10                  15

Val Lys Asn Gln Asn
            20

<210> SEQ ID NO 4
<211> LENGTH: 20
<212> TYPE: PRT
<213> ORGANISM: Ananas comosus

<400> SEQUENCE: 4

```
Val Pro Gln Ser Ile Asp Trp Arg Asp Ser Gly Ala Val Thr Ser Val
  1               5                  10                  15

Lys Asn Gln Gly
            20

<210> SEQ ID NO 5
<211> LENGTH: 20
<212> TYPE: PRT
<213> ORGANISM: Ananas comosus

<400> SEQUENCE: 5

Val Pro Gln Ser Ile Asp Trp Arg Asn Tyr Gly Ala Val Thr Ser Val
  1               5                  10                  15

Lys Asn Gln Gly
            20
```